United States Patent
Grupp et al.

(10) Patent No.: US 7,026,330 B2
(45) Date of Patent: Apr. 11, 2006

(54) METHODS FOR TREATMENT OF ACUTE LYMPHOCYTIC LEUKEMIA

(75) Inventors: Stephan A. Grupp, Havertown, PA (US); Valerie I. Brown, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 10/453,056

(22) Filed: May 30, 2003

(65) Prior Publication Data
US 2004/0039010 A1 Feb. 26, 2004

Related U.S. Application Data

(60) Provisional application No. 60/384,245, filed on May 30, 2002.

(51) Int. Cl.
*A61K 31/44* (2006.01)
(52) U.S. Cl. .................................... 514/291
(58) Field of Classification Search ................ 514/291; 530/387.1
See application file for complete search history.

(56) References Cited

U.S. PATENT DOCUMENTS

| 4,401,653 | A |   | 8/1983  | Eng               |         |
|-----------|---|---|---------|-------------------|---------|
| 4,885,171 | A | * | 12/1989 | Surendra et al.   | 424/122 |
| 5,100,899 | A | * | 3/1992  | Calne             | 514/291 |
| 5,206,018 | A |   | 4/1993  | Sehgal et al.     |         |
| 5,362,718 | A |   | 11/1994 | Skotnicki et al.  |         |

FOREIGN PATENT DOCUMENTS

EP          0 525 960 A1 *  2/1993

OTHER PUBLICATIONS

Ditonno, P., et al., "Regulatory effects of interleukin-7 on renal tumor infiltrating lymphocytes", Urol. Res., vol. 20: p. 205-210, (1992).
Touw, I., et al., "Interleukin-7 Is a Growth Factor of Precursor B and T Acute Lymphoblastic Leukemia", Blood, vol. 75: p. 2097-2101, (1990).
Wagner, E.F., et al., "A Pivotal Role of Cyclin D3 and Cyclin-Dependent Kinase Inhibitor p27 in the Regulation of IL-2-, IL-4-, or IL-10-Mediated Human B Cell Proliferation", J. Immunology, 161: 1123-1131 (1998).
Majewski, M., et al., "The immunosuppressive macrolide RAD inhibits growth of human Esptein-Barr virus-transformed B lymphocytes in vitro and in vivo: A potential approach to prevention and treatment of posttransplant lymphoproliferative disorders", PNAS, vol. 97: p. 4285-4290, (2000).
Bauer, S.R., et al., "Clonal Relationship of the Lymphoblastic Cell Line P388 to the Macrophage Cell Line P388D1 as Evidenced by Immunoglobulin Gene Rearrangements and Expression of Cell Surface Antigens", J. Immunology, vol. 136: p. 4695-4699 (1986).
Dawe, C.J., et al., "Morphologic and Biologic Expression of a Lymphoid Neoplasm of the Mouse In Vivo and In Vitro", Scientific Proceedings, vol. 33: p. 603 (1957).
Eng., C.P., et al., "Activity of Rapamycin (AY-22, 989) Against Transplanted Tumors", The Journal of Antibiotics, vol. 37: p. 1231-1237, (1984).
Muthukkumar, S., et al., "Rapamycin, a Potent Immunosuppresive Drug, Causes Programmed Cell Death in B Lymphoma Cells", Transplantation, vol. 60: p. 264-270 (1995).
Aagaard-Tillery, K.M., et al., "Inhibition of Human B Lymphocyte Cell Cycle Progression and Differentiation by Rapamycin", Cellular Immunology vol. 156: p. 493-507, (1994).
Calastretti, A., et al., "Rapamycin increases the cellular concentration of the BCL-2 protein and exerts an anti-apoptotic effect", European J. of Cancer 37: 2121-2128 (2001).

(Continued)

*Primary Examiner*—Elli Peselev
(74) *Attorney, Agent, or Firm*—Dann Dorfman Herrell and Skillman; Kathleen D. Rigaut

(57) ABSTRACT

Methods for treating patients having an early B cell derived acute lymphoblastic leukemia with rapamycin or a derivative thereof are provided. Also provided are methods for treating patients having an early B cell derived acute lymphoblastic leukemia with rapamycin or a derivative thereof in combination with an IL-7 inhibitor. Finally methods for preventing GVHD in ALL patients following a bone marrow transplant are disclosed.

11 Claims, 6 Drawing Sheets

OTHER PUBLICATIONS

Hidalgo, M., et al., "The rapamycin-sensitive signal transduction pathway as a tartet for cancer therapy", Oncogene, vol. 19: 6680-6686 (2000).

Kay, J.E., et al., "Inhibition of T and B lymphocyte proliferation by rapamycin", Immunology, vol. 72: p. 544-549 (1991).

Coleman, A.E., "Cytogenetic analysis of the biopotential murine pre-B cell lymphoma, P388, and its derivative macrophage-like tumor, P388D1, using SKY and CGH", Leukemia, vol 13: p. 1592-1600 (1999).

ASCO Daily News, "New Molecular-Based Paradigms for Drug Development Yield Promising Results", wysiwyg://107/http://www.asco.org/prof/and/2000/tue/NewTargets.htm; Accessed Jan. 17, 2002.

Appasamy, Biological and Clinical Implications of Interleukin-7 and Lymphopoiesis, Cytokines, Cellular and Molecular Therapy (1999), vol. 5, pp. 25-39.

Barata et al., Interleukin-7 promotes survival and cell cycle progression of T-cell acute lymphoblastic leukemia cells by down-regulating the cyclin-dependent kinase inhibitor $p27^{kip1}$, Blood (2001), vol. 98, No. 5, pp. 1524-1531.

Benjamin, et al., B Cell IL-7. Human B Cell Lines Constitutively Secrete IL-7 and Express IL-7 Receptors, Journal of Immunology (1994), vol. 152, pp. 4749-4757.

Bierer et al., Two distinct signal transmission pathways in T lymphocytes are inhibited by complexes formed between an immunophilin and either FK506 or rapamycin, PNAS (1990), vol. 87, pp. 9231-9235.

Brown et al., A mammalian protein targeted by G1-arresting rapamycin-receptor complex, Nature (1994), vol. 369, pp. 756-758.

Brunn et al., Phosphorylation of the Translational Repressor PHAS-1 by the Mammalian Target of Rapamycin, Science (1997), vol. 277, pp. 99-101.

Burnett et al., RAFT1 phosphorylation of the translational regulators p70 S6 kinase and 4E-BP1, PNAS (1998), vol. 95, pp. 1432-1437.

Calne et al., Rapamycin for Immunosupression in Organ Allografting, The Lancet (1989), p. 227.

Castedo et al., Mammalian Target of Rapamycin (mTOR): Pro-and Anti-Apoptotic, Cell Death and Differentiation (2002), vol. 9, pp. 99-100.

Cavazzana-Calvo et al., Gene Therapy of Human Severe Combined Immunodeficiency (SCID)-X1 Disease, Science (2000), vol. 288, pp. 669-672.

Cavazzana-Calvo et al., Gene therapy of severe combined immunodeficiencies, The Journal of Gene Medicine (2001), vol. 3, pp. 201-206.

Chen et al., A Putative Sirolimus (Rapamycin) Effector Protein, Biochemical and Biophysical Research Communications (1994), vol. 203, No. 1, pp. 1-7.

Chessells, Relapsed Lymphoblastic Leukaemia in Children: A continuing Challenge, British Journal of Haematology (1998), vol. 102, pp. 423-438.

Cronin et al., Role of μ Heavy Chain in B Cell development. I. Blocked B Cell Maturation But Complete Allelic Exclusion in the Absence of Igα/β, The Journal of Immunology, (1998), vol. 161, pp. 252-259.

Dadi et al., Interleukin-7 Receptor Mediates the Activation of Phosphatidylinosital-3 Kinase in Human B-Cell Precursors, Biochemical and Biophysical Research Communications (1993), vol. 192, No. 2, pp. 459-454.

Dadi et al., Activation of Phosphatidylinositol-3 Kinase by Ligation of the Interleukin-7 Receptor on Human Thymocytes, J. Clin. Invest. (1993), vol. 92, pp. 1559-1563.

Dadi et al., Activation of Phosphatidylinositol-3 Kinase by Ligation of the Interleukin-7 Receptor Is Dependent on Protein Tyrosine Kinase Activity, Blood (1994), vol. 84, No. 5, pp. 1579-1586.

Degiannis et al., Rapamycin Inhibits the In Vitro Release of Soluble CD23 by SAC/IL-2/IL-4- Activated Human Peripheral Blood B Lymphocytes, Transplantation (1995), vol. 59, No. 7, pp. 1076-1079.

Foss, et al., Frequent Expression of IL-7 Gene Transcripts in Tumor Cells of Classical Hodgkin's Disease, American Journal of Pathology, (1995), vol. 146, No. 1, pp. 33-39.

Dittel et al., The Growth response to IL-7 During Normal Human B Cell Ontogeny Is Restricted to B-Lineage Cells Expressing CD34, The Journal of Immunology (1995), vol. 154, pp. 58-67.

Dumont et al., Relationship Between Multiple Biologic Effects of Rapamycin and the Inhibition of pp70S6 Protein Kinase Activity. Analysis in Mutant Clones of a T Cell Lymphoma, Journal of Immunology (1994), vol. 152, pp. 992-1003.

Elit, CCI-779 Wyeth, Current Opinion in Investigational Drugs (2002), vol. 3, No. 8, pp. 1249-1253.

Ettenger et al., Safety and Efficacy of TOR Inhibitors in Pediatric Renal Transplant Recipients, American Journal of Kidney Diseases (2001), vol. 38, No. 4, pp. S22-S28.

Fischer, Severe combined immunodeficiencies (SCID), Clin. Exp. Immunol. (2000). vol. 122, pp. 143-149.

Fischer, Primary Immunodeficiency Diseases: Natural Mutant Models for Study of the Immune System, Scandinavian Journal of Immunology (2002), vol. 55, pp. 238-241.

Garber, Rapamycin's Resurrection: A New Way to Target the Cancer Cell Cycle, Journal of the National Cancer Institute (2001), vol. 93., No. 20, pp. 1517-1519.

Gaynon et al., Survival after Relapse in Childhood Acute Lymphoblastic Leukemia, Cancer (1998), vol. 82, No. 7, pp. 1387-1395.

Goodfellow et al., RET Gene and Its Implications for Cancer, Journal of the National Cancer Institute (1995), vol. 87, No. 20, pp. 1515-1523.

Guba et al., Rapamycin inhibits primary and metastatic tumor growth by antiangiogenesis: involvement of vascular endothelial growth factor, Nature Medicine (2002), vol. 8, No. 2, pp. 128-135.

Hacein-Bey-Abina et al., Sustained Correction of X-Linked Severe Combined Immunodeficiency by Ex Vivo Gene Therapy, The New England Journal of Medicine (2002), vol. 346., No. 16, pp. 1185-1193.

Hacein-Bey-Abina et al., A Serious Adverse Event after Successful Gene Therapy for X-Linked Severe Combined Immunodeficiency, The New England Journal of Medicine (2003), vol. 348., No. 3, pp. 255-256.

Hayakawa et al., B Lymphocyte Developmental Lineages, Annals of the New York Academy of Sciences(1997), vol. 815, p. 15-29.

Hidalgo et al., The rapamycin-sensitive signal transduction pathway as a target for cancer therapy., Oncogene (2000), vol. 19, pp. 6680-6686.

Hofmeister et al., Interleukin-7:physiological roles and mechanisms of action, Cytokine & Growth Factor Reviews (1999), vol. 10, pp. 41-60.

Huang et al., Mechanisms of resistance to rapamycins, Drug Resistance Updates (2001), vol. 4, pp. 378-391.

Huang et al., Inhibitors of mammalian target of rapamycin as novel antitumor agents:From bench to clinic, Current Opinion in Investigational Drugs (2002), vol. 3, No. 2, pp. 295-304.

Ichihara et al, Oncogene-linked in situ immunotherapy of pre-B lymphoma arising in Eμ/ret transgenic mice, British Journal of Cancer (1995), vol. 71, pp. 808-813.

Iwamoto et al., Preferential development of pre-B lymphomas with drastically down-regulated N-myc in the Eμ/ret transgenic mice, Eur. J. Immunol. (1991), vol. 21, pp. 1809-1814.

Karawajew et al., Inhibition of in vivo spontaneous apoptosis by IL-7 correlates with Bcl-2 up-regulation, cortical/mature immunophenotype, and better early cytoreduction of childhood T-cell acute lymphoblastic leukemia., Blood (2000), vol. 96, No. 1, pp. 297-306.

Kuo et al., Rapamycin selectively inhibits interleukin-2 inhibition of p70 S6 kinase., Nature (1992), vol. 358, pp. 70-73.

Li et al., Suboptimal Cross-linking of Antigen Receptor Induces Syk-dependent Activation of p70S6 Kinase through Protein Kinase C and Phosphoinositol 3-Kinase, The Journal of Biological Chemistry (1999), vol. 274, No. 14, pp. 9812-9820.

LeBien, Fates of human B-cell precursors, Blood (2000), vol. 96, No. 1, pp. 9-23.

Loken et al., Flow Cytometric Analysis of Human Bone Marrow. II. Normal B Lymphocyte Development, Blood (1987), vol. 70, No. 5, pp. 1316-1324.

MacDonald et al., Clinical Pharmacokinetics and Therapeutic Drug Monitoring of Sirolimus, Clinical Therapeutics (2000), vol. 22, Suppl. B, pp. B101-B121.

Morris, Rapamycin: FK506's fraternal twin or distant cousin?, Immunology Today (1991), vol. 12, pp. 137-140.

Mosmann, Rapid Colorimetric Assay for Cellular Growth and Survival: Application to Proliferation and Cytotoxicity Assays, Journal of Immunological Methods (1983), vol. 65, pp. 55-63.

Page et al., Interleukin-7 activates p56$^{lck}$ and p59$^{fyn}$, two tyrosine kinases associated with the p90 interleukin-7 receptor in primary human T cells, Eur. J. Immunol. (1995), vol. 25, pp. 2956-2960.

Pribyl et al., Interleukin 7 independent development of human cells, PNAS (1996), vol. 93, pp. 10348-10353.

Raught et al., The target of rapamycin (TOR) proteins, PNAS (2001), vol. 98, No. 13, pp. 7037-7044.

Renard et al., Proliferation of MIELIKI a novel t(7;9) early pre-B acute lymphoblastic leukemia cell line is inhibited concomitantly by IL-4 and IL-7, Leukemia (1995), vol. 9, pp. 1219-1226.

Sakata et al., Involvement of a rapamycin-sensitive pathway in CD40-mediated activation of murine B cells in vitro, Immunology Letters (1999), vol. 68, pp. 301-309.

Sato et al., Stromal Cells Provide Signals Different from Cytokines for STAT5 Activation in Hematopoietic Cells, Cell Structure and Function (2001), vol. 26, pp. 95-101.

Saunders et al., Rapamycin in transplantation: A review of the evidence, Kidney International (2001), vol. 59, pp. 3-16.

Schreiber, Chemistry and biology of the Immunophilins and Their Immunosuppressive Ligands, Science (1991), vol. 251, pp. 283-287.

Seckinger et al., Activation of src Family Kinases in Human Pre-B Cells by IL-7, The Journal of Immunology (1994), vol. 153, pp. 97-109.

Smart et al., Inhibition of Interleukin 7 Receptor Signaling by Antigen Receptor Assembly, J. Exp. Med. (2000), vol. 191, No. 4, pp. 737-742.

Stoddart et al., The role of preBCR, the interleukin 7 receptor, and homotypic interactions during B-cell development, Immunological Reviews (2000), vol. 175, pp. 47-58.

Touw et al., Interleukin-7 is a Growth Factor of Precursor B and T Acute Lymphoblastic Leukemia, Blood (1990), vol. 75, No. 11, pp. 2097-2101.

Uckun et al., Interleukin 7 receptor engagement stimulated tyrosine phosphorylation, inositol phospholipid turnover, proliferation, and selective differentiation to the CD4 lineage by human fetal thymocytes, PNAS (1991), vol. 88, pp. 6323-6327.

Van Der Plas et al., Interleukin-7 signaling in human B cell precursor acute lymphoblastic leukemia cells and murine BAF3 cells involves activation of STAT1 and STAT5 mediated via the interleukin-7 receptor αchain, Leukemia (1996), vol. 10, pp. 1317-1325.

Vogler et al., Pre-B-Cell Leukemia. A New Phenotype of Childhood Lymphoblastic Leukemia, The New England Journal of Medicine, (1978), pp. 872-878.

Wasserman, Differential Expression of Blk and Ret Tyrosine Kinases During B Lineage Development is Dependent on Ig Rearragement, The Journal of Immunology, 1995), vol. 155, pp. 644-651.

Wasserman et al., The Evolution of B Precursor Leukemia in the Eμ-ret Mouse, Blood (1998), vol. 92, No. 1, pp. 273-282.

Wei et al., Murine Pro-B Cells Require IL-7 and It's Receptor Complex to Up-Regulate IL-7Rα, Terminal Deoxynucleotidyltransferase and cμ Expression, Journal of Immunology (2000), vol. 164, pp. 1961-1970.

Weng et al., Regulation of the p70 S6 Kinase by Phosphorylation in Vivo, The Journal of Biological Chemistry (1998) vol. 273, No. 26, pp. 16621-16629.

West et al., Translational induction of the c-myc oncogene via activation of the FRAP/TOR signalling pathway, Oncogene (1998), vol. 17, pp. 769-780.

Wicker et al., Suppression of B cell activation by cyclosporin A, FK 506 and rapamycin, Eur. J. Immunol. (1990), vol. 20, pp. 2277-2283.

Wuchter et al., In vitro susceptibility to dexamethasone- and doxorubicin-induced apoptotic cell death in context of maturation stage, responsiveness to interleukin 7, and early cytoreduction in vivo in childhood T-cell acute lymphoblastic leukemia., Blood (2002), vol. 99, No. 11, pp. 4109-4115.

Yada et al., IL-7 Prevents Both Caspase-Dependent and -Independent Pathways that Lead to the Spontaneous Apoptosis of i-IEL, Cellular Immunology (2001), vol. 208, pp. 88-95.

Yehuda et al., Activation of the Recombination Activating Gene 1 (RAG-1) Transcript in Bone Marrow of Senescent C57BL/6 Mice By Recombinant Interleukin-7, Journal of Gerontology (1999), vol. 54A, No. 4, pp. B143-B148.

Zeng et al., The Fetal Origin of B-Precursor Leukemia in the Eμ-ret Mouse, Blood (1998) vol. 92, No. 10, pp. 3529-3536.

* cited by examiner

RFP 2045 Pre- Treatment    RFP 2045 Post-Treatment

METHODS FOR TREATMENT OF ACUTE LYMPHOCYTIC LEUKEMIA

CROSS REFERENCE TO RELATED APPLICATION

This application claims priority under 35 U.S.C. §119(e) to U.S. Provisional Patent Application No. 60/384,245 filed on May 30, 2002, the entire disclosure of which is incorporated by reference herein.

GOVERNMENT RIGHTS

Pursuant to 35 U.S.C. §202(c), it is acknowledged that the U.S. Government has certain rights in the invention described herein, which was made in part with funds from the National Institutes of Health, Grant Nos. NIH 5-T32-CA-09165, NIH-T32-HL-07150, NIH K-K12-CA-76931, and NIH R01 CA82156.

FIELD OF THE INVENTION

Methods for using rapamycin or derivatives thereof, in the treatment of a patient with early B cell derived acute lymphoblastic leukemia (ALL) are disclosed. Methods are also provided for the treatment of a patient afflicted by an early B cell-derived ALL with rapamycin or a derivative thereof in combination with an IL-7 inhibitor. Also provided are methods for preventing GVHD in ALL patients following bone marrow transplantation.

BACKGROUND OF THE INVENTION

All publications, patent applications, patents, and other references mentioned herein are incorporated by reference in their entirety.

Many childhood malignancies are lymphoid in origin and arise from transforming events that occur in early B cell progenitors [Vogler, 1978]. Understanding normal B cell development affords the opportunity to learn how the transformation process subverts normal B cell signaling mechanisms. In turn, this information provides the means to design novel targeted chemotherapeutics. In normal B cell development, rearrangement of the immunoglobulin heavy chain gene occurs during pro-B cell stages (reviewed in [LeBien, 2000]). The late pro-B cell normally is in the process of completing the rearrangement of heavy chain (V to DJ) joining. If successful gene re-arrangement occurs, then the cell will progress through the pre-B cell stage, producing IgM heavy chain ($\mu$) protein and undergoing a burst of proliferation. Pre-B cells are identified by expression of cytoplasmic $\mu$ protein and assembly of the pre-B cell receptor (pre-BCR) complex [Loken, 1987]. If the B cell precursor fails to make a productive VDJ arrangement at both alleles, cell death will occur, which is the fate of the vast majority of (>90%) early pre-B cells [Li, 1993]. Survival, apoptotic and differentiation signals, provided by host of molecules (e.g. pre-BCR complex [Cronin, 1998], adhesion molecule receptors and cytokine receptors [Stoddart, 2000]), are tightly regulated to maintain B-lymphocyte homeostasis. An imbalance in these signals can lead to lymphoid malignancies.

The B cell at the late pro-B/early pre-B transition is a common target of transformation. In the clinical setting, acute lymphoblastic leukemia (ALL) cells derived from early B-lineage cells are loosely referred to as "pre-B ALL", although the majority of these cells are more correctly defined as pro-B cells with no cytoplasmic $\mu$ expression.

Much work has been done to phenotypically and biochemically characterize classes of leukemia and lymphoma using a variety of models including transgenic mice [Vogler, 1978; Ichihara, 1995]. The RET protein is a tyrosine kinase expressed during the development of pro-B cells, and RET expression is down regulated when $\mu$ protein is expressed during the pre-B cell stages of B cell development [Wasserman, 1995]. E$\mu$-RET+ transgenic mice constitutively express activated RET tyrosine kinase under the control of the $\mu$ enhancer (E$\mu$), driving B-lineage restricted expression of the activated RET protein. Between 4 and 8 months of life, E$\mu$-RET+ transgenic mice develop lymphoblastic lymphoma/leukemia manifested by massive adenopathy, splenomegaly and bone marrow replacement [Goodfellow, 1995; Iwamoto, 1991; Wasserman, 1998; Zeng, 1998]. The malignant cells are B220+/CD43lo/surface IgM−, and the majority are cytoplasmic $\mu$- (J. Fang, unpublished data). Thus, the B-lymphoid malignancies that arise in E$\mu$-RET+ mice are derived from the late pro-B to early pre-B cell stage of development [Hayakawa, 1997]. The E$\mu$-RET+ transgenic mouse provides a developmentally targeted model of ALL that is useful in preclinical evaluation of novel therapeutic strategies.

Cytokines play an important role in promoting and controlling normal B cell development (reviewed in [Appasamy, 1999; Fry, 2002]) and are involved in malignant transformation of lymphoid precursor cells [Page, 1995]. Overall, IL-7 acts at three levels in normal lymphoid cells (reviewed in [Fry, 2001; Hofmeister, 1999; Appasamy, 1999]. It 1) acts as a trophic factor by preventing apoptosis [Lu, 1999]; 2) controls lineage-specific developmental programs such as V(D)J rearrangement [Nutt, 2001; Veiby, 1997]; and 3) stimulates proliferation of targeted cells [Corcoran, 1996]. IL-7 was originally described as a B cell growth factor secreted by bone marrow stromal cells [Henney, 1989]. Subsequently, IL-7 was found to promote the growth of pro-T cells as well, produced by cortical epithelial cells in the thymus. It is absolutely required for normal murine T and B cell development as well as human T cell development (reviewed in [Hofmeister, 1999]). IL-7 acts as a modulator of low affinity peptide-induced proliferation, a central feature of homeostatic regulation of T cell populations in humans [Fry, 2001; Tan, 2001]. Although not absolutely required for B cell development in humans, IL-7 still plays an important role in human B cell development [Pribyl, 1996; Dittel, 1995]. IL-7 provides a survival signal to early B lymphoid precursors [Smart, 2000]. IL-7 signals through the IL-7 receptor (IL-7R), a heterodimer receptor composed of two subunits, the gamma common ($\gamma_c$) chain (CD132) and the IL-7R$\alpha$ chain (CD127) [Page, 1995]. The $\gamma_c$ chain is shared by other cytokine receptors including IL-2R, IL-4R, IL-9R, IL-15R, and IL-21R, while the IL-7R$\alpha$ chain is unique to the IL-7 receptor, whose expression varies with different stages of lymphoid development [Sudo, 1993; Armitage, 1991]. IL-7R$\alpha$ chain is expressed from the early pro-B cell stage through the pre-B cell stage [Sudo, 1993]. IL-7 promotes the formation of a functional pre-B cell receptor (pre-BCR) in pro-B cells and the transition to pre-B cells. Down-regulation of IL-7 signaling in pre-B cells serves as a trigger for initiating apoptosis during negative selection of B cells with unproductive Ig rearrangements [Frishman, 1993]. PreBCR+ B cells have a proliferative advantage over PreBCR− B cells in response to low or limiting concentrations of IL-7 because of increased response to IL-7 [Fleming, 2001]. Finally, IL-7R$\alpha$ expression ceases very late in the late pre-B cell stage [Smart, 2000]. When IL-7 engages the IL-7R on pro-B cells, IL-7R tyrosine phosphorylation and PI turnover occurs, resulting in clonal proliferation [Uckun, 1991]. Because the IL-7R itself has no intrinsic kinase activity, IL-7-induced phosphorylation occurs as a result of recruiting intracellular kinases, including the JAK/STAT system [Sato, 2001; van der Plas, 1996] as well as activation of PI-3 kinase [Dadi, 1993; Dadi, 1993; Dadi, 1994] and src family kinases [Seckinger, 1994].

IL-7 has been associated with certain malignancies [Karawajex, 2000; Wuchter, 2002; Touw, 1990; Barata, 2001]). Karawajew et al., reported that IL-7 rescues T cell ALL lymphoblasts from apoptosis [Karawajew, 2000]. Wuchter, et al., found that IL-7 greatly inhibited drug-induced apoptosis in T cell ALL cells [Wuchter, 2002]. IL-7 plays a role in T-cell ALL, modulating cell cycle regulators [Touw, 1990; Barata, 2001]. IL-7 leads to the down regulation of p27kip1, causing the induction of Bcl-2 leading to proliferation of leukemic T cells [Barata, 2001]. Also, IL-7 induces progression through the cell cycle; it leads to increased expression of CyclinD2/CyclinA, upregulation of CDK4 and CDK2, and phosphorylation of Rb protein [Barata, 2001]. IL-7 may be associated with Hodgkin's disease. Foss, et al., have shown elevated serum levels in a significant number of patients with Hodgkin's disease prior to treatment [Foss, 1995]. Also, IL-7 is constitutively secreted in American EBV+ Burkett's lymphoma as well as EBV+ cell lines [Benjamin, 1994]. There are several reports of IL-7 stimulating growth of human precursor B cell ALL cells [Renard, 1995]. Although there are reports of B cell lineage ALL subclones that have had decreased dependence on IL-7 and Flt-3L secreted by the BM microenvironment [Shah, 2001], the role of these cytokines in the development or progression of progenitor B cell lymphoid malignancies has not been fully elucidated [Touw, 1990; van der Plas, 1996].

Rapamycin, a mTOR inhibitor, is a macrolide antibiotic produced by *Streptomyces hygroscopicus* which was originally described as an antifungal agent. It is known to inhibit the growth of fungi, including *Candida albicans* and *Microsporum gypseum*. Methods for the preparation of rapamycin and characterization of its antibiotic activity were described in U.S. Pat. No. 3,929,992. Martel et al. reported that rapamycin possesses immunosuppressive properties which are effective for controlling experimental allergic encephalitis and adjuvant arthritis (1977, Canadian Journal of Physiological Pharmacology 55:48). Rapamycin has also been shown to inhibit rejection of allograft transplantation in vivo (Calne, et al., 1989, Lancet 2:227; Morris and Meiser, 1989, Medicinal Science Research 17:609). It was found that rapamycin inhibits the induction of activation and proliferation of mature T and B cells [Kay, 1991; Sakata, 1999; Morris, 1991]. Consequently, rapamycin was approved by the FDA for use as an immunosuppressive agent after solid organ transplant ([Ettenger, 2001] and reviewed in [Saunders, 2001]). There is also evidence that mTOR inhibitors, e.g. rapamycin, may inhibit the growth of and/or induce apoptosis in a wide variety of tumor types ([Eng, 1984; Douros, 1981; Houchens, 1983] and reviewed in [Huang, 2002; Huang, 2001; Elit, 2002; Hidalgo, 2000; Garber, 2001]). It has been shown that rapamycin alone [U.S. Pat. No. 4,885,171] or in combination with picibanil [U.S. Pat. No. 4,401,653] possess antitumor properties. [Calne, 1989; Schreiber, 1991; Saunders, 2001]. The development of second generation macrolides, derivatives of rapamycin, has therefore been focused on the antitumor activity of this class of drugs.

Rapamycin inhibits the activation of the mammalian Target of Rapamycin (mTOR). mTOR is a serine/threonine kinase and functions as a sensor to ensure that the cell is in an appropriate nutritional state prior to committing to cell division [Dennis, 2001; Schmelzle, 2000]. Through its interactions with other proteins, including p70S6 kinase [Dumont, 1994; Kuo, 1992], PI-3K [Castedo, 2002], and p34cdc2, mTOR regulates several processes including cell growth, initiation and elongation of mRNA translation [Castedo, 2002; Brunn, 1997; Burnett, 1998], ribosome synthesis [West, 1998], expression of metabolism-related genes, amino acid import, autophagy, and cytoskeletal reorganization (reviewed in [Raught, 2001]). By inhibiting mTOR, rapamycin mimics growth factor withdrawal, characterized by cell cycle arrest at $G_1$ and inhibition of protein synthesis [Chen, 1994; Brown, 1994]. Upon entering the cell, rapamycin must bind to the FK-binding Protein12 (FKBP12) in order to be active [Chen, 1994; Brown, 1994]. It is this FKBP12/rapamycin complex that blocks mTOR activity [Chen, 1994; Brown, 1994]. In T cells, rapamycin shifts the balance between activation and inhibition of cyclin-dependent kinases (CDK) towards inhibition by blocking the down-regulation of p27kip1 [Nourse, 1994].

IL-2 is an important growth factor for T cells. IL-2 selectively phosphorylates p70S6 kinase [Kuo, 1992]. P70S6 kinase activates ribosomal proteins S6 and S17 to promote protein synthesis [Dumont, 1994; Kuo, 1992], and p70S6 kinase's activity is inhibited by rapamycin [Price, 1992; Frost, 1996; Patel, 1996]. IL-2 normally activates cyclin E/Cdk2 complexes by eliminating p27kip1 [Nourse, 1994]. This down-regulation of p27kip1 is key to IL-2-driven cell cycle progression. Thus, rapamycin causes inactivation of p70S6 kinase, cyclin E, Cdk2, and p34cdc2 [Kuo, 1992; Nourse, 1994; Terada, 1993; Flanagan, 1993]. Cells with low levels of p27kip1 are resistant to rapamycin, and T cells from p27kip1−/− knockout mice exhibit a significant resistance to rapamycin inhibition [Luo, 1996]. Thus, rapamycin inhibits mTOR and subsequently inhibits protein synthesis as well as cell cycle progression at the $G_1$ to S transition. In addition to affecting IL-2 mediated signaling, rapamycin blocks the IL-7 mediated down-regulation of p27kip1 and in vivo phosphorylation of Rb protein in leukemic T cells [Barata, 2001; Ponce-Castaneda, 1995]. The persistent expression of p27kip1 in rapamycin-treated normal and leukemic T cells suggests that mTOR is a critical component of the signaling pathway that targets p27kip1 for ubiquitin-dependent proteolysis [Pagano, 1995; Morice, 1993]. Although not as well studied as in T cells, rapamycin has growth inhibitory effects in B cells in vitro [Wicker, 1990; Sakata, 1999]. Rapamycin inhibits secretion of sCD23, an autocrine B cell growth factor [Degiannis, 1995]. Crosslinking of BCR leads to p70S6 kinase activation, triggering protein synthesis via activation of ribosomal proteins [Li, 1999]. Calastretti, et al., compared rapamycin treated human follicular B cell lymphoma cell lines (characterized by high levels of BCL-2 in a steady state) to cell lines with lower BCL-2 expression level, and they found that cell lines with high expression of BCL-2 showed more inhibition than cell lines with low BCL-2 expression [Calastretti, 2001]. Harada, et al., found that p70S6 kinase phosphorylates BAD, inactivating it [Harada, 2001].

SUMMARY OF THE INVENTION

In accordance to the present invention, methods for treating a patient with early B cell ALL comprising the administration to the patient a therapeutically effective amount of rapamycin or an derivative thereof are provided. The patient may be newly diagnosed with early B cell ALL or may be experiencing refractory or relapsed early B cell ALL.

In one aspect of the invention, the method for treating a patient with early B cell ALL comprises the administration of a therapeutically effective amount of rapamycin or an derivative thereof in combination with a therapeutically effective amount of an IL-7 inhibitor, such as an anti-IL-7 antibody, simultaneously or sequentially.

In another aspect, the method for treating a patient with early B cell ALL comprises the administration of a therapeutically effective amount of rapamycin or an derivative thereof in combination with a therapeutically effective amount of at least one anti-cancer agent.

In yet another aspect of the present invention, methods for preventing or treating graft vs. host disease following a bone marrow transplant in children with relapsed or refractory ALL are provided. An exemplary method entails administration of a therapeutically effective dose of rapamycin for a suitable time period following bone marrow transplant to prevent onset of GVHD. Such method may also optionally include administration of other conventional immunosuppressant agents, including without limitation, cyclosporine and prednisone. The inventive methods should improve the prognosis for children with refractory or relapsed ALL.

DETAILED DESCRIPTION OF THE INVENTION

Figure 1:
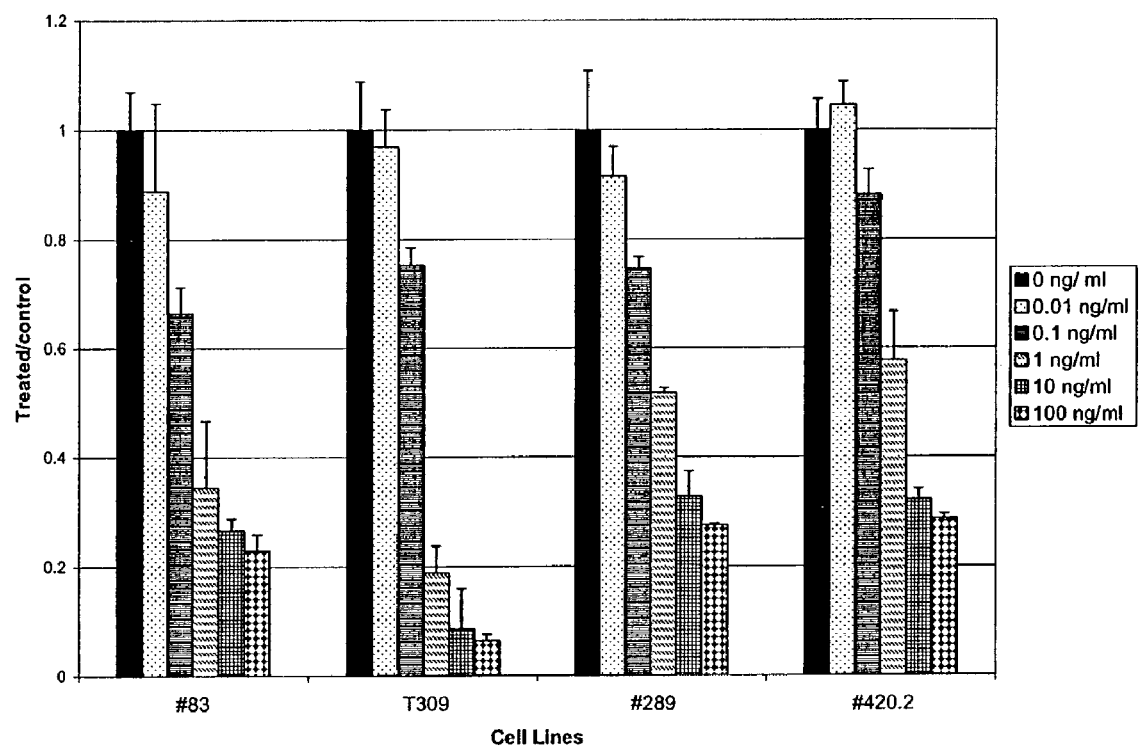
FIG. 1 is a graph showing that rapamycin inhibits proliferation of ALL cell lines. $2\times10^4$ Eμ-RET+ transgenic mouse derived cell lines, #83, T309, #289, #420.2, were cultured with 1 U/ml rmIL-7 and increasing concentrations of rapamycin (0 ng/ml to 100 ng/ml). After 3 days incubation, cell proliferation was assessed using MTT. All samples were done in triplicate. Bars represent mean of the relative absorbance of triplicate cultures, and error bars represent standard error of the mean.

A balance between survival and apoptotic signals regulates B cell development. These signals are tightly regulated by a host of molecules including IL-7. Loss of normal homeostatic control can lead to leukemia arising from progenitor B cells. Pre B cell leukemia is the most common form of human pediatric cancer and there is a profound need for novel methods for the treatment of this disease.

Mammalian Target of Rapamycin (mTOR) inhibitors (e.g. rapamycin and its derivatives) were initially developed as immunosuppressive agents. According to the present invention, it was found that rapamycin inhibits growth of B precursor ALL cell lines in vitro, an apoptotic response that is reversible by IL-7. It is also found that rapamycin demonstrates in vivo activity in Eμ-RET+ transgenic mice which develop pre-B leukemia/lymphoma: Eμ-RET+ transgenic mice with overt disease treated with rapamycin as a single agent daily showed an almost 3-fold increase in survival as compared to untreated symptomatic littermates. These results demonstrate that mTOR inhibitors, e.g., rapamycin and its derivatives are effective agents against leukemia, and that one of the growth signals inhibited by this class of drugs in precursor B cells is IL-7-mediated.

The present invention is therefore directed to methods for administration of rapamycin or derivatives thereof in the treatment of patients with early B cell ALL. The term "early B cells" as used herein refers to late pro to early pre B cells, which are generally B220+, CD34lo, and cytoplasmic IgM negative (IgM⁻) in mice and C19+, CD10 and/or 34+, and IgM⁻ in humans. The present invention is also directed to methods for using rapamycin or derivatives thereof in combination with IL-7 inhibitors in the treatment of patients with early B cell ALL. Mammals or patients afflicted with early B cell ALL include those with newly diagnosed early B cell ALL and those with refractory or relapse of early B cell ALL.

In yet another aspect, the present invention provides methods for administration of rapamycin and derivatives thereof for post-bone marrow transplant graft vs. host disease prophylaxes in children with ALL. Such a method should increase overall and event-free survival of such patients.

I. Pharmaceutical Preparation of Rapamycin and Derivatives Thereof and Methods for Administration of the Same Rapamycin, a macrocyclic triene antibiotic produced by *Streptomyces hygroscopicus* is described in U.S. Pat. No. 3,929,992. Methods for preparing rapamycin or its derivatives and pharmaceutical compositions comprising the same are well know in the art and have been disclosed in the following exemplary list of U.S. Pat. Nos. 5,258,389; 5,262,423; 5,665,772; 5,985,325; 6,004,973; 6,197,781; 6,200,985; 6,277,983; 6,342,507; and 6,503,883; the entire contents of which are incorporated herein by reference.

Specifically, when rapamycin or a derivative thereof is employed as an therapeutic agent in the treatment of early B cell ALL, it can be formulated neat or with a pharmaceutical carrier for administration to a patient in need thereof. The pharmaceutical carrier may be solid or liquid.

A solid carrier can include one or more substances which may also act as flavoring agent, lubricants, solubilizers, suspending agents, fillers, glidants, compression aids, binders or table-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized composition. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agent, colors, viscosity regulators, stabilizers or osmo-regulators. Suitable examples of liquid carriers for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and iopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The therapeutic agent can also be administered orally either in liquid or solid composition form.

Rapamycin or derivatives thereof may also be administered rectally in the form of a conventional suppository. Rapamycin or derivatives thereof may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Rapamycin or derivatives thereof may be administered topically as a solution, cream, or lotion by formulation with pharmaceutically acceptable vehicles containing 0.1–5 percent, preferably 2%, of active compound.

Methods for the administration of rapamycin or its derivatives in the treatment of human subjects having a variety of different disorders have been previously disclosed in U.S. Pat. Nos. 4,401,653; 4,885,171; 5,080,889; 5,204,229; 5,321,009; 5,387,589; 5,516,781; 5,665,728; and European Patent Application 525,960 A1, the entire contents of which are incorporated herein by reference.

Particularly, rapamycin or derivatives thereof may be administered to a patient with an early B cell ALL by any means known and as frequently as is necessitated to maintain a therapeutically effective dose. Therapeutic effective doses and regimens for the treatment of such patients are known to those of skill in the art and may be determined based on a number of criteria which include, but are not limited to, the patient's condition, age, sex, the stage of disease, and the patient's medical history. The dosage requirements also vary with the particular compositions employed and the route of administration. Based on the results obtained in the standard pharmaceutical test procedure, projected daily doses of the active compound, e.g., rapamycin or an derivative thereof, would be determined. Treatment will generally be initiated with small dosages less than the optimum dose of the active compound. Thereafter the dosage is increased until the optimum effect under the circumstances is reached; precise dosages for oral, parenteral, topic, transdermal, or rectal administration will be determined by the administering physician based on experience with the individual subject treated. In general, rapamycin or a derivative thereof is most desirably administered at a concentration that will generally afford effective results, e.g., suppressing leukemia cell growth or prolonging survival, without causing any harmful or deleterious side effects, and can be administered either as a single unit dose, or if desired, the dosage may be divided into convenient subunits administered a suitable times throughout the day.

It is also anticipated that a therapeutically effective dosage of rapamycin or an derivative thereof for the treatment of an early B cell ALL patient may exceed that used in the treatment of, for example, a transplant patient.

Also within the scope of the present invention are methods for treating a patient with an early B cell ALL using rapamycin or an derivative thereof in combination with an IL-7 inhibitor. IL-7 inhibitors include, but are not limited to, IL-7 specific antibodies (both polyclonal and monoclonal antibodies) and fragments thereof.

The encoding sequence of human and murine IL-7 and antibodies (both polyclonal and monoclonal antibodies) immunoreactive with IL-7, are disclosed in U.S. Pat. No. 5,714,585, the entire disclosure of which is incorporated herein by reference. Suitable anti-IL-7 antibodies for use in the methods of the invention include, but are not limited to, ab9325 and ab9628 from Novus Biologicals, Inc., Littleton, Colo., 80160.

For particular uses, it may be desirable to use fragments of anti-IL-7 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to IL-7 polypeptide in vitro, and selecting antibody display libraries in phage or similar vectors (for instance, through use of immobilized or labeled IL-7 protein or peptide). Genes encoding polypeptides having potential IL-7 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the IL-7 gene sequences to identify proteins which bind to IL-7.

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to the present invention, rapamycin or an derivative thereof and, optionally, an IL-7 inhibitor may be administered simultaneously or sequentially to a patient for treating early B cell ALL. Optionally, the methods of the invention may also include administration of anti-cancer agents which include, without limitation, at least one anti-cancer agent selected from the group consisting of cisplatin, carboplatin, oxaliplatin, radiation, CPT-11, paclitaxel, 5-flourouracil, leucovorin, epothilone, gemcitabine, UFT, herceptin, cytoxan, dacarbaxine, ifosfamide, mechlorethamine, melphalan, chlorambucil, anastrozole, exemstane, carmustine, lomustine, methotrexate, gemcitabine, cytarabine, fludarabine, bleomycin, dactinomycin, daunorubicin, doxorubicin, idarubicin, docetaxel, vinblastine, vincristin, vinorelbine, topotecan, lupron, megace, leucovorin, Iressa, flavopiridol, immunomotherapeutic agents, ZD6474, SU6668, valspodar, and an IL-7 inhibitor.

The following examples are provided to illustrate certain embodiments of the invention. They are not intended to limit the invention in any way.

EXAMPLES

Example I

The mTOR Inhibitor Rapamycin is Active Against B-precursor Leukemia in vitro and in vivo, an Effect Which is Modulated by IL-7 Mediated Signaling Material and Methods Cell Preparation and Cell Culture Conditions. A single cell suspension of bone marrow or lymph nodes from leukemic Eμ-RET+ transgenic mice was prepared [Wasserman, 1998]. These ALL cells were maintained at 37° C. with 5% $CO_2$ in RPMI-1640, L-Glutamine, 10 mM HEPES, 1 mM Sodium Pyruvate, 100 μM non-essential amino acids, 100 U/ml penicillin, 100 μg/ml streptomycin (GibCo-BRL, Rocksville, Md.), 50 μM 2-mercaptoethanol (FisherScientific, Fair Lawn, N.J.)+10% Fetal Calf Serum (HyClone, Logan, Utah)+10% Calf Serum (HyClone, Logan Utah) (C20 media) with 10 U/ml IL-7. Cell surface markers on these cells were determined by flow cytometry as described previously [Wasserman, 1998], and the phenotype was stable in culture over time.

Proliferation Assays. Cells were cultured in IL-7-free C20 media for 24 hours. For in vitro culture studies, $1-2 \times 10^4$ cells/well were cultured in triplicate in flat bottom 96-well plates with increasing concentrations of rapamycin (Calbiochem, La Jolla, Calif.) (0 ng/ml to 100 ng/ml) and recombinant mouse IL-7 (rmIL-7) (Leinco Technologies, Inc., St. Louis, Mo.) (0 U/ml to 30 U/ml) for 3–4 days. Cell growth was assayed using methyl-thiazole-tetrazolin (MTT) [Mosmann, 1983]. After removing 50 μl media from each well, 10 μl MTT, 5 mg/ml, (Sigma, St. Louis, Mo.) was added to each sample and incubated for 4 hours. 150 μl 1% HCL/Isopropanol was added to each sample and mixed vigorously until all crystals dissolved. Absorbance was measured at $OD_{595}$ using microplate spectrophotometer (Benchmark Microplate Reader, Bio-Rad Laboratories, Hercules, Calif.). Results are expressed as mean of absolute absorbance number$_{treated\ sample}$ divided by the mean of absolute absorbance number$_{control\ sample}$. Results >1 indicates proliferation whereas results <1 indicates growth inhibition.

Apoptosis Assay. $0.5-1 \times 10^5$ cells/ml were plated in C20 media with increasing concentrations of rapamycin and rmIL-7 and incubated for 3 days. Levels of exposed phosphotidylserine on viable cells were measured using the ApoAlert Annexin V detection kit (Clontech, Palo Alto, Calif.). Cells were incubated with FITC-conjugated Annexin V, and log fluorescence intensity was analyzed by flow cytometry using a FACScan cytometer (Becton-Dickinson, Franklin Lakes, N.J.).

Crude Lysate Preparation and Immunoblotting. $5 \times 10^6$ cells were incubated in C20 media with or without 10 U/ml IL-7, 100 ng/ml rapamycin or 10 U/ml IL-7+100 ng/ml rapamycin for 4 hours. After harvesting, cells were washed with ice cold PBS and then lysed in 100 μl of 1% Triton-X containing protease and phosphatase inhibitors (1 μg/ml apoprotinin, 1 μg/ml leupeptin, 1 mM $Na_3OV_4$, 1 mM NaF, 0.1 mM AEBSF) at 4° C. for 5 minutes. Crude lysates were obtained by centrifugation (12,000 rpm at 4° C. for 20 minutes). Protein concentrations were determined using Bio-Rad Protein assay kit (Bio-Rad Laboratories, Hercules, Calif.). Equal amounts of protein were analyzed by 4–12% Tris-Bis gel electrophoresis and transferred to PVDF membranes (NuPage Invitrogen, Carlsbad, Calif.). Specific proteins were detected with anti-Phosphor-p70S6 kinase (Thr389) and anti-total p70S6 kinase antibodies (Cell Signaling Technologies, Beverly, Mass.) diluted in TTBS (1:500). Immunodetection was performed with horseradish peroxidase-conjugated anti-rabbit IgG and then developed by chemoluminescence (Amersham Pharmacia Biotech, Piscataway, N.J.). Immunoblots were stripped for reprobing by incubating immunoblots in stripping buffer (100 mM 2-mercaptoethanol, 2% sodium dodecyl sulphate, 62.5 mM Tris-HCl pH 6.7) for 30 minutes in 37° C. water bath with occasional agitation. Blots were then washed with TTBS at RT for 2×10 minutes, reblocked in 5% Blotto (Santa Cruz Biotechnology, Inc., Santa Cruz, Calif.) in TBS for 1 hr at RT. Specific proteins were immunoblotted and detected as above.

Transgenic Mouse Studies. Eμ-RET+ transgenic mice express RFP/RET fusion gene under the control of IgH enhancer (Eμ-RET+). Eμ-RET+ transgenic mice were generated on C57BL/6×DBA2 background and then Eμ-RET+ mice were bred into BALB/C background [Wasserman, 1998]. Mice were assessed three times a week for overt signs of disease (enlarged lymph nodes, organomegaly, and anemia). When symptomatic, mice were randomized to daily intraperitoneal treatment with rapamycin (Wyeth-Ayerst Pharmaceuticals, Inc., Philadelphia, Pa.) or no treatment. Prior to randomization, easily accessible enlarged lymph nodes were biopsied for cell culture and further in vitro study. Peripheral blood for CBC with differential (HemaVet 850FS, Cell Technologies, Oxford, Conn.) and pK studies was obtained by eye bleeding at days 0, 7, 14 and then every other week until death. Peripheral blood as well as single cell suspension from bone marrow, lymph nodes and/or spleen was obtained at death. Weights were monitored three times a week. 5 mg/kg rapamycin was administered IP daily. Animals were sacrificed when moribund. Event free survival (EFS) was determined from onset of disease until death, and analyzed using STATA 7.0 (STATA Corporation, College Park, Tex.).

Results

Rapamycin Inhibits Proliferation of Eμ-RET+ Transgenic Derived Leukemia/Lymphoma Cell Lines. In order to evaluate the mTOR inhibitor, rapamycin, in models of progenitor B cell malignancies, we first investigated the effect of rapamycin on ALL cell lines in vitro. The Eμ-RET+ transgenic mouse derived cell lines, #83, T309, #289, and #420.2 were cultured with 1 U/ml rmIL-7 and with increasing concentrations of rapamycin (0 ng/ml to 100 ng/ml). Cell proliferation was assessed using MTT after three days of incubation. FIG. 1 shows profound inhibition of the growth of ALL lines in culture with nanogram concentrations of rapamycin. At 1 ng/ml concentration, there was a >40% inhibition of growth in all cell lines tested. There was a >70% inhibition of growth at 100 ng/ml. These results were obtained after 3 days of culture and allow differentiation of the effect of 1 ng/ml and 100 ng/ml rapamycin. By 4–5 days of culture, all of cells treated even with the lower concentration of rapamycin were dead (data not shown). By comparison, typical serum levels of patients on rapamycin were 8–12 ng/ml, showing that this effect is pharmacologically relevant [MacDonald, 2000]. Rapamycin was tested in a large variety of murine and human T and B cell lines including Jurkat, BJAB, J558L, Nalm 6, Nalm 16, and A20 (ATCC, Manassas, Va. 20108) and had similar effects on growth inhibition (data not shown). In contrast, the proliferation of the neuroblastoma cell line SK-NA-S was unaffected by rapamycin at doses up to 100 ng/ml (data not shown).

Figure 2:
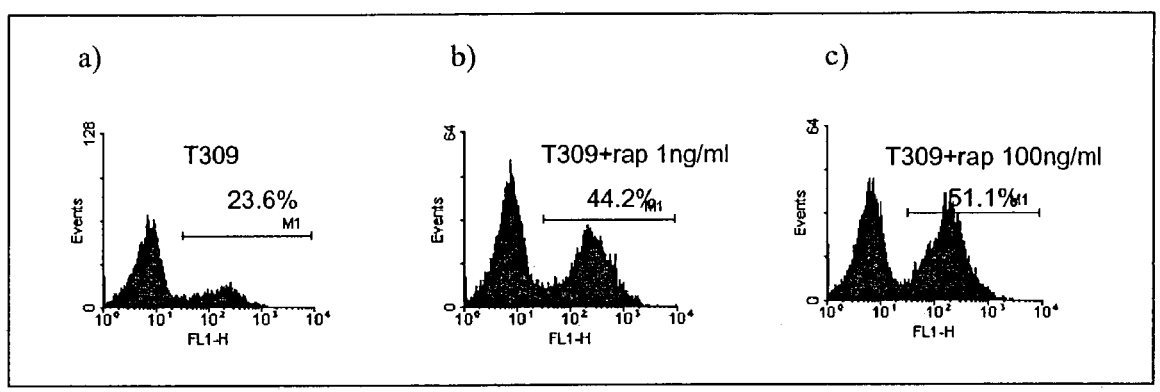
FIG. 2 is a graph demonstrating that rapamycin induces apoptosis of ALL cell lines. Eμ-RET+ transgenic mouse derived pro-B cell line T309 was treated with increasing concentrations of rapamycin (0 ng/ml to 100 ng/ml) for 48 hours. Cells were assessed for apoptotic response by labeling with FITC-conjugated Annexin V. Percentages of apoptotic cells are indicated. Flow cytometric histograms show a) untreated; b) 1 ng/ml rapamycin; and c) 100 ng/ml rapamyin. Peak on right represents FITC-conjugated Annexin V positive cells.

Rapamycin Induces Apoptosis. In order to see if the rapamycin-sensitive cells undergo apoptosis, we treated the pro-B ALL cell line T309 cells with increasing concentrations of rapamycin for 72 hours, and then labeled the cells with Annexin V-FITC. The results of these Annexin V assays show that rapamycin induces apoptosis in these ALL cell lines (FIG. 2). At baseline, 24% of T309 cells were labeled with Annexin V, increasing to 44% after treatment with 1 ng/ml rapamycin and to 51% with 100 ng/ml of rapamycin. These results demonstrate that the inhibitory effect of rapamycin is due to induction of apoptosis.

Figure 3:
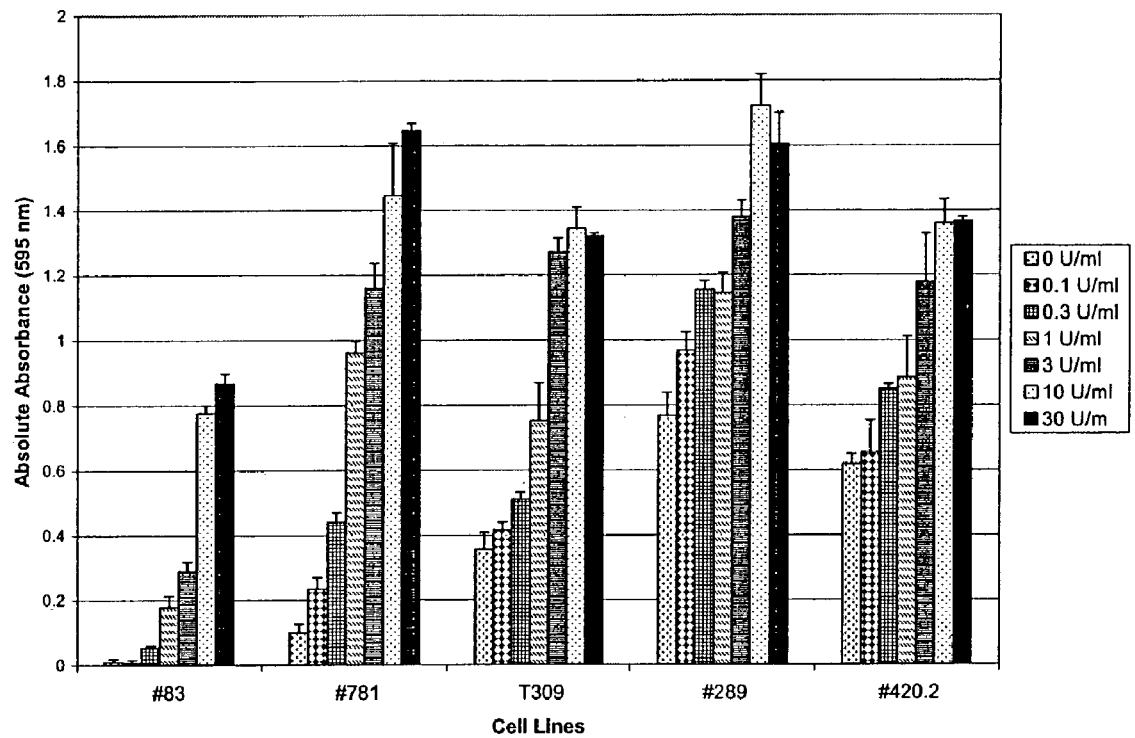
FIG. 3 is a graph showing that rmIL-7 stimulates proliferation of ALL cell lines in the absence of stroma. $1\times10^4$ Eμ-RET+ transgenic mouse derived cell lines, #83, #781, T309, #289, #420.2, were cultured with increasing concentrations of rmIL-7 (0 U/ml to 30 U/ml). After 4–5 days incubation, cell proliferation was assessed using MTT. All samples were done in triplicate. Bars represent mean of the absolute absorbance of triplicate cultures, and error bars represent standard error of the mean.

IL-7 Stimulates Proliferation of Eµ-RET+ Derived Leukemia/Lymphoma Cell Lines. We then explored the effect of IL-7 signaling in this system. Many of the cell lines used in these studies are derived from the Eµ-RET+ transgenic mouse. These cell lines are almost all IL-7 responsive, and some are IL-7 dependent. As seen in FIG. 3, leukemia/lymphoma cell lines derived from Eµ-RET+ transgenic mice are IL-7 responsive. Although all the cell lines tested are IL-7 responsive, some grow in the absence of IL-7, while others are IL-7 dependent. Cell lines #83, #781 and T309 show IL-7 dependence, while cell lines #289 and #420.2 are IL-7 responsive, but do not require this early B cell cytokine for growth in culture. A20 is a mature B cell line, whose proliferation is not affected by IL-7 (data not shown). Cell proliferation increased with increasing concentrations of rmIL-7 ranging from a 2.2 fold increase proliferation in cell lines #289 and #420.2 and 3.7 fold increase in cell line T309 to a 16 fold increase in #781 cell line and an almost 100 fold increase in cell line #83. The response to rmIL-7 appears to plateau between 10–30 U/ml rmIL-7. None of these cell lines requires stroma for proliferation in culture. Thus, the leukemia cell lines derived from Eµ-RET+ transgenic mice are stromal independent but remain IL-7 responsive, with some of these cell lines still requiring IL-7 for proliferation while others have become IL-7 independent.

Figure 4:
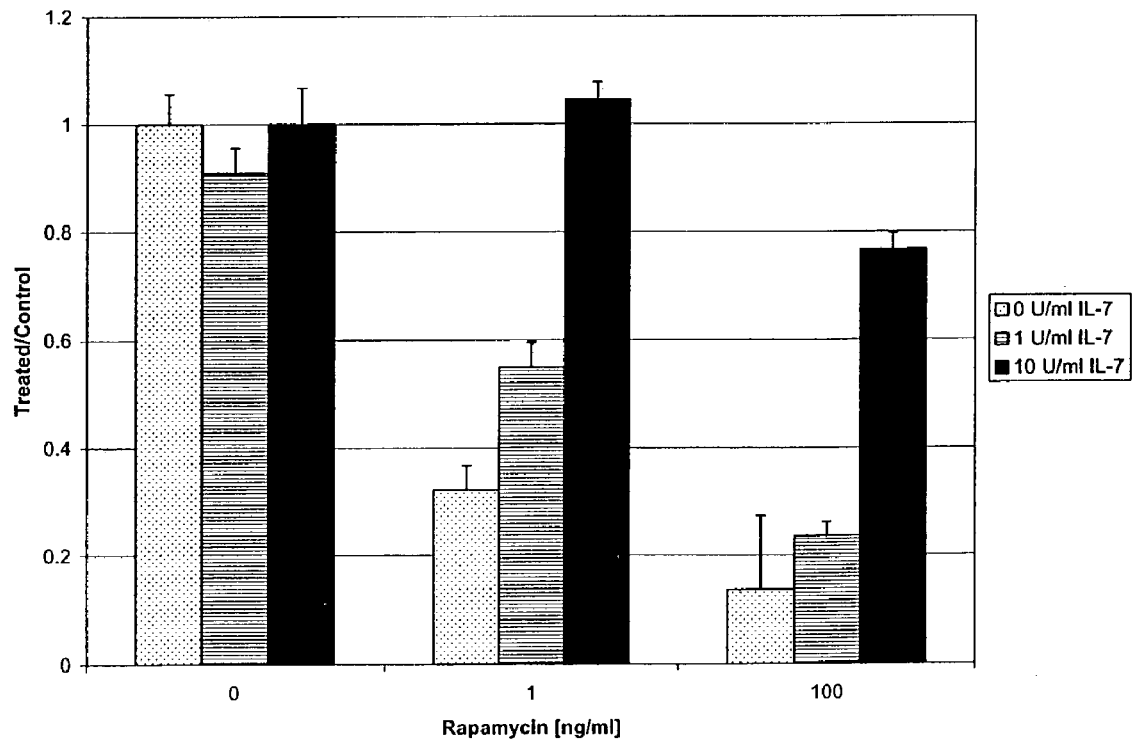
FIG. 4 is a graph showing that rmIL-7 reverses rapamycin-induced growth inhibition of ALL cell line #289. $2\times10^4$ cells were cultured with increasing concentrations of rapamycin (0, 1, or 100 ng/ml) and increasing concentrations of rmIL-7 (0, 1 or 10 U/ml) for 3 days. Cell proliferation was assessed using MTT. All samples were done in triplicate. Bars represent mean of the treated/control (as described in materials and methods) of triplicate cultures, and error bars represent standard error of the mean.

IL-7 Reverses the Inhibitory Effect of Rapamycin. A stroma-independent response to IL-7 is one of the earliest changes noted in pro-B cells from Eµ-RET+ transgenic mice, an effect that is seen even in fetal development and long before malignant transformation of the cells (J. Fang, unpublished data). This augmented stroma-independent response may provide a "first hit" that may be analogous to that seen in the SCID-X1 gene experience [Hacein-Bey-Abina, 2003]. Because of these data and the importance of IL-7 in lymphoid development, we hypothesized that IL-7 treatment might reverse the inhibitory effect of rapamycin. This proved to be the case, as shown in FIG. 4. Cells were cultured with increasing concentrations of rapamycin (0, 1 or 100 ng/ml) and rmIL-7 (0, 1 or 10 U/ml) for three days and then proliferation assessed using MTT. As seen in FIG. 4, cell line #289 is almost completely inhibited by rapamycin with a dose-dependent rescue by IL-7. In the presence of low dose rapamycin (1 ng/ml), rmIL-7 at 10 U/ml completely reverses rapamycin-induced growth inhibition. In the presence of 100 ng/ml rapamycin, rmIL-7 at 10 U/ml only partially reverses (by almost 80% of baseline) rapamycin's effect on cell growth. The profound inhibition obtained with low doses of rapamycin (1 ng/ml) is completely reversed with 10 U/ml IL-7. This reversal is seen in cell lines that are IL-7 dependent, IL-7 responsive (i.e. cells that grow in the absence of IL-7 but increase proliferation when exposed to IL-7), and even cell lines that do not exhibit a response to IL-7 treatment in the absence of concurrent treatment with rapamycin. Similar results were seen in human ALL cell lines as well (data not shown). These data reveal that this cytokine pathway is targeted by mTOR inhibitors, and that IL-7 pathway is a potential therapeutic target for signal transduction inhibition.

Figure 5:
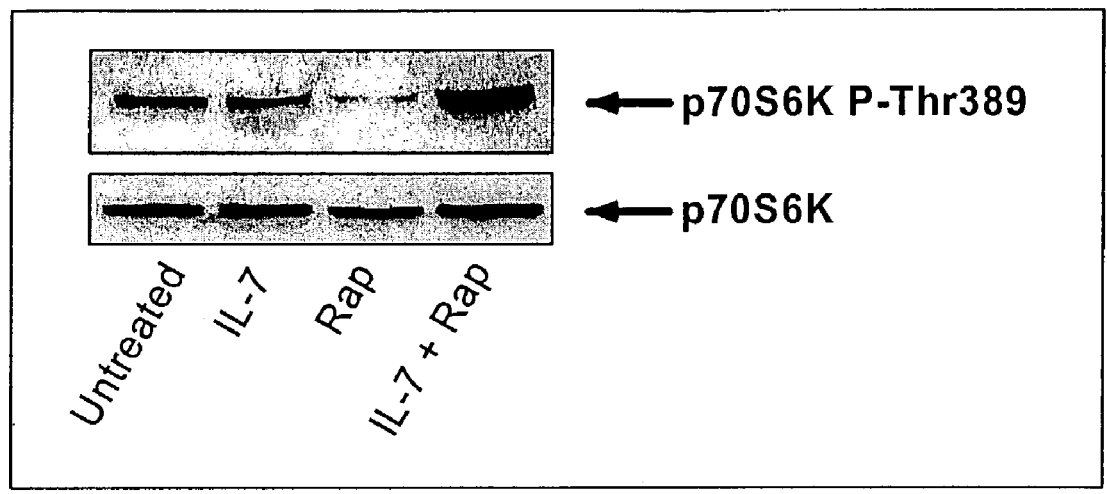
FIG. 5 is a gel picture showing the effect of rapamycin and IL-7 on phosphor-p70S6 kinase. $5\times6^{10}$ #289 ALL cells were cultured with 10 U/ml IL-7 and 100 ng/ml rapamycin for 4 hours. Top: immunoblot of phosphor-p70S6 kinase (Thr389); Bottom: total p70S6 kinase protein from the same blot. 100 μg were loaded per lane.

IL-7 Restores the Rapamycin-induced Dephosphorylation of p70S6 Kinase. In order to study the mechanism of the ability of IL-7 to reverse the inhibitory effect of rapamycin on ALL cells, we used immunoblotting of cell lysates to detect proteins and phosphoproteins downstream of mTOR and the IL-7R. To determine signaling intermediates potentially cross-regulated by rapamycin and IL-7, we detected phosphor-p70S6 kinase (Thr389) and p70S6 kinase total protein levels in the ALL cell line #289 after treatment with rapamycin +/−IL-7. After treatment for 4 hours with rapamycin, this cell line showed a profound decrease in phosphor-p70S6 kinase, an effect reversed by IL-7 (FIG. 5, upper panel). As expected, p70S6 kinase total protein levels were unchanged by treatment with rapamycin, IL-7 or a combination of rapamycin+IL-7 (FIG. 5, bottom panel).

Figure 6:
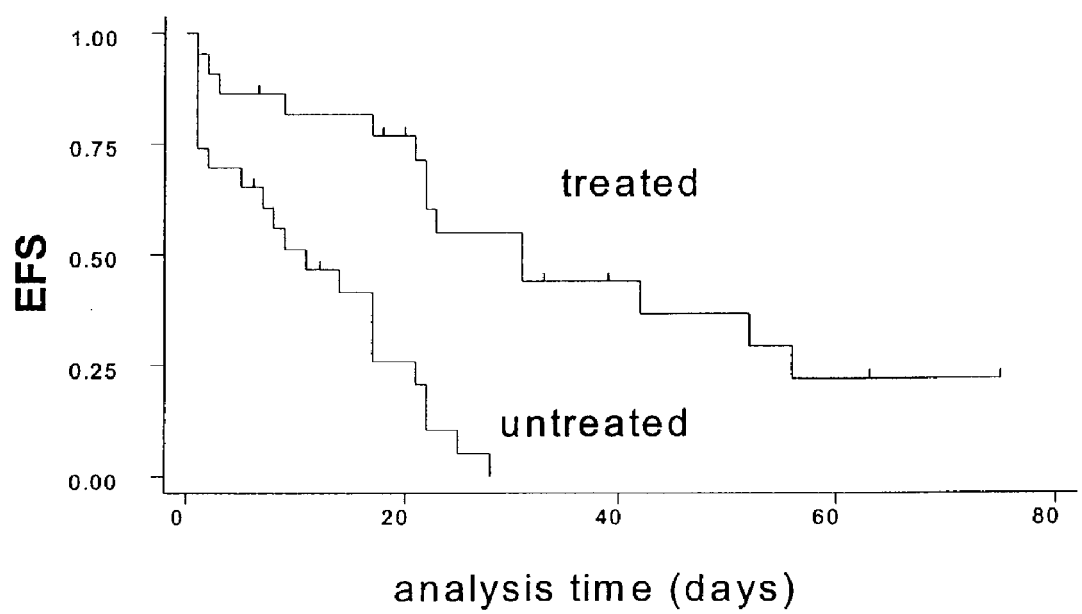
FIG. 6 is a graph showing that rapamycin as a single agent prolongs survival by almost 3 fold of leukemic mice with advanced disease. Eμ-RET+ transgenic mice with overt disease were treated daily intraperitoneally with rapamycin (5 mg/kg/dose) as described in materials and methods. This Kaplan-Meier analysis of event free survival shows the fraction of animals surviving after onset of disease. Rapamycin extends survival in leukemic mice by 3 fold in treated mice as compared to untreated mice. The average time from diagnosis to death is 30 days (N=34) in treated mice and 12 days (N=23) in untreated mice (p<0.001).

Rapamycin as a Single Agent Extends Survival and Normalizes Elevated Peripheral White Blood Cell Counts in Leukemic Mice with Advanced Disease. In order to study the effect of rapamycin in vivo, Eµ-RET+ transgenic mice were treated daily with rapamycin once they manifested signs of advanced disease, including enlarged lymph nodes, hepatosplenomegaly, and weight loss. When compared to untreated littermates, rapamycin extends survival in rapamycin treated Eµ-RET+ transgenic mice with advanced disease almost 3-fold as seen in the Kaplan-Meyer curve in FIG. 6. The average time from diagnosis to death is 12 days for untreated mice (range: 5–39 days, N=23), vs. 30 days for rapamycin-treated mice (range: 9–77 days, N=34) ($P<0.001$).

Figure 7A:
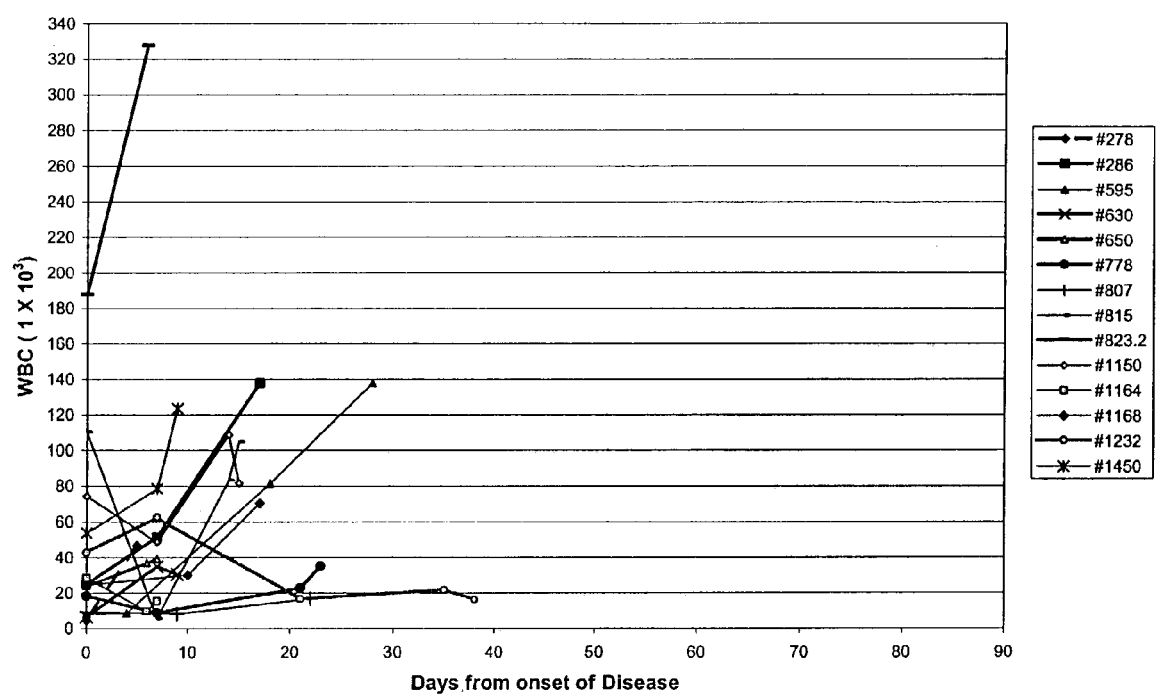
FIGS. 7a and 7b are graphs showing that rapamycin rapidly normalizes elevated peripheral WBC in leukemic mice with advanced disease. Peripheral blood was obtained by eye bleeding for a CBC at days 0, 7, 14, and then every other week as well as at the time of sacrifice. CBC values are not available at later time points in the untreated group because all of these mice have died of their disease long before day 30, which is the median survival point of the treated group. Graphs represent WBC from diagnosis to death of a) untreated mice and b) rapamycin-treated mice.
Figure 7B:
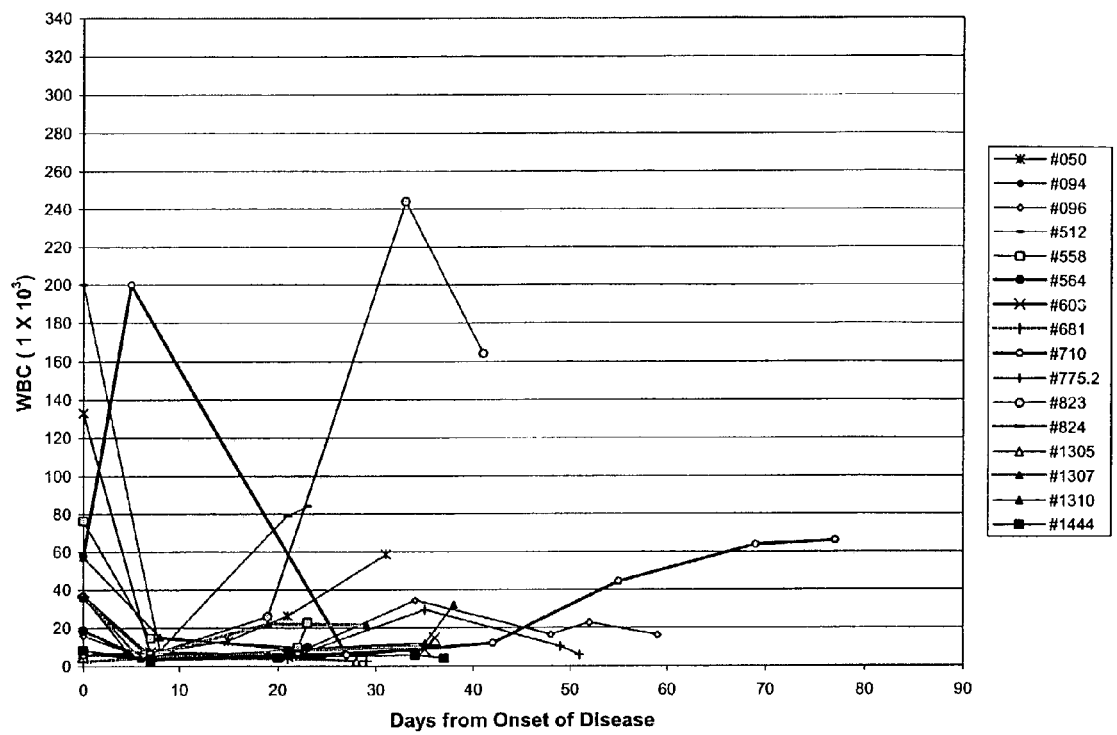
Figure 8:
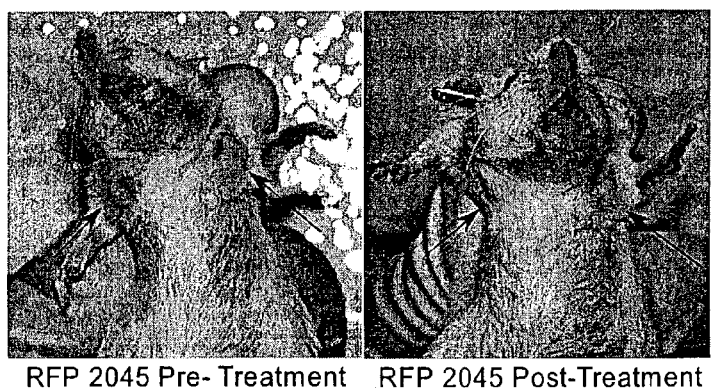
FIG. 8 is a picture showing that mTOR inhibitor, rapamycin, significantly reduces leukemic adenopathy. Left panel shows a leukemic Eμ-RET+ transgenic mouse with overt disease. This mouse has significant cervical and axillary adenopathy as indicated by the arrows. Right panel, the same mouse 14 days post treatment with rapamycin shows significant reduction in tumor burden.

We monitored the complete blood counts and weights in rapamycin-treated versus untreated mice. Peripheral CBCs were measured in treated and untreated mice at 0, 7, and 14 days and then every 14 days for the duration of the experiment. Weights were monitored three times a week for the duration of the experiment. In addition to extending survival in Eµ-RET+ transgenic mice, rapamycin also normalized the peripheral white blood cell count (WBC). In the untreated mice, WBC increased progressively until the animals were sacrificed (Table I; FIG. 7a), while WBC in the rapamycin-treated mice normalized within 7–10 days of instituting therapy (Table I; FIG. 7b). However, by the time of sacrifice, the mean WBC of the treated mice was above normal with a mean of 31.0 (range: 2.5–164). The mean hemoglobin and platelet counts of the untreated mice as compared to the rapamycin treated mice were not significantly different (Table I). The weights of the treated versus untreated groups were not significantly different, and the mice receiving rapamycin did not suffer from weight loss. Thus, rapamycin in these mice was well tolerated, reducing tumor burden without causing significant anemia and/or thrombocytopenia. The positive response to rapamycin was also clinically apparent with rapid decreases in nodal masses (FIG. 8). The mouse shown in FIG. 8 represents the typical course seen with mice treated with rapamycin. This mouse presented with a WBC of 28.8, reaching a nadir of 3.2 after 14 days of rapamycin treatment.

TABLE I

Summary of CBC of Untreated versus Rapamycin-treated Mice over Time

| | Mean at D0 (range) | | Mean at D7 (range) | | Mean at D14 (range) | | Mean at d21 (range) | | Mean at sacrifice (range) | |
|---|---|---|---|---|---|---|---|---|---|---|
| | untreated | treated | untreated | treated | untreated | treated | untreated | treated | untreated | treated |
| WBC ($\times 10^3$/μl)* | 44.2 (4.7–188) | 47.8 (2.3–133) | 54.3 (5.8–328) | 18.5 (2.9–200) | 101 (70.5–138) | N/D | N/D | 14.3 (4.0–78.7) | 84.6 (15.5–328) | 31.0 (2.5–164) |
| Hgb (g/dL)† | 13.2 (9.8–16.5) | 12.5 (8.7–15) | 11.4 (7.2–17.1) | 12.8 (7.3–18.3) | N/D | N/D | N/D | 12.1 (7.6–16.7) | 11.2 (7.7–15.6) | 12.5 (8.4–16.6) |
| Plt ($\times 10^3$/μl)‡ | 573 (219–1203) | 695 (229–1084) | 580 (156–1600) | 584 (251–1663) | N/D | N/D | 449 (325–544) | 526 (171–772) | 445 (135–768) | 573 (147–1057) |
| Weight (grams) | 29.3 (S.D = 3.9) | 25.6 (S.D. = 3.0) | N/D | N/D | 30.0 (S.D. = 2.9) | 28.1 (S.D. = 2.9) | | | 30.3 (S.D. = 4.8) | 28.10 (S.D. = 4.7) |

*normal range for WBC in mice is 1.8–10.7 × $10^3$/μl
†normal range for Hemoglobin (Hgb) in mice is 11.0–15.1 g/dL
‡normal range for platelet (Plt) in mice is 592–2972 × $10^3$/ml
Note: These normal ranges were determined by Cell Technologies, Oxford CT and based on Schalm's Veterinary Hematology Manual, 5th Edition, B. Feldman, J. Zinkl, N. Jain, Eds., Lippincott, Williams & Wilkins, Philadelphia, PA, 2000(74).

Discussion

Leukemia is a very common childhood malignancy. The majority of pediatric acute lymphoblastic leukemia (ALL) arises from transforming events that occur in early precursor B lineage cells. Although the prognosis for pediatric ALL has improved dramatically over the past two decades, the prognosis for refractory and relapsed ALL remains poor [Gaynon, 1998; Chessells, 1998]. Thus, newer, targeted agents need to be identified and integrated into the present cytotoxic chemotherapy regimens. Using animal models to study leukemogenesis as well as drug development, particularly of agents targeting inhibition of signal transduction, has become a mainstay in devising novel strategies for cancer treatment. Using the Eμ-RET+ transgenic mouse as a model for lymphoblastic lymphoma/leukemia, we report here 3 significant findings: 1) The mTOR inhibitor, rapamycin, inhibits proliferation of leukemia cells in vitro; 2) rapamycin is active as a single agent in vivo against ALL; and 3) the rapamycin-induced growth inhibition is reversible by rmIL-7, demonstrating that IL-7 mediated signaling is involved in the response of pre-B ALL cells to rapamycin.

These data have provided the framework upon which we have designed clinical trials using mTOR inhibitors in patients with relapsed or refractory leukemia and lymphoblastic lymphoma. Rapamycin is a well studied mTOR inhibitor with immunosuppressive and anti-tumorigenic properties. Rapamycin was initially developed as an immunosuppressive agent because it was found to inhibit the induction and proliferation of mature T and B cells [Morris 1999]. Subsequently, rapamycin is commonly used for immunosuppression after solid organ transplant in adult and pediatric patients. In preclinical studies, rapamycin inhibited IL-7 mediated cell cycle progression and cellular proliferation of T-cell ALL cells [Barata, 2001]. Rapamycin inhibited metastatic solid tumor growth and angiogenesis in preclinical studies [Guba, 2002]. Our data demonstrate that mTOR inhibitors are also active agents against pre-B ALL at a dose that is well within the achievable physiologic serum levels in humans.

We investigated the effect of IL-7 in this system because 1) IL-7 plays a role in cell survival and differentiation during the early stages of B cell development (reviewed in [LeBien, 2000]), 2) malignant transformation occurs at the pro-B/early pre-B cell transition in our leukemia mouse model [Wasserman, 1998, Fang, 2002] and 3) the IL-7 receptor shares the γ common chain with IL-2 receptor [Corcoran, 1996]. IL-7 causes the proliferation of pro-B cells [Wei, 2000] and can upregulate RAG 1 expression in lymphoid precursors [Yehuda, 1999]. IL-7 appears to be essential for the development of normal B and T cells in mice. IL-7 and IL-7Rα knockout mice have profound defects in B cell development (reviewed in [Appasamy, 1999]). In humans, IL-7 causes proliferation of early precursor B cells, but is not essential for B cell development [Pribyl, 1996]. Aberrant IL-7 expression has been associated with certain malignancies. Recently, two cases of T cell leukemia have developed in patients with X-linked severe combined immunodeficiency (SCID-X1) after receiving autologous CD34+ bone marrow cells transduced ex vivo with γc chain gene [Hacein-Bey-Abina, 2003]. The remaining eight patients continue to have functioning T, B and NK cell function for >3 years, but they are being closely monitored for the advent of similar disease [Hacein-Bey-Abina, 2002; Cavazzana-Calvo, 2000]. SCID-X1 manifested by deficient T and natural killer cell production and abnormal B cell function occurs as a result of a mutation in the γc chain (reviewed in [Fischer, 2002; Fischer, 2000]). This phenotype is mainly a consequence of defective IL-7 and IL-15 signaling [Cavazzana-Calvo, 2001]. The T cell leukemia developing in these two SCID-X1 patients after ex vivo transduction of the γc chain gene into CD34+ BM cells may be partially a result of increased cytokine signaling and an enhanced activation state in the lymphocytes, the status of which renders the lymphocytes leukemia-prone and susceptible to a "second hit". We see a similar picture in the leukemia-prone Eμ-RET+ mouse model (J. Fang, unpublished data).

Our observation that IL-7 reverses the apoptotic response of rapamycin on these ALL cells is supported by data reported by others. Karawajew et al. [Karawajex, 2000] have shown that IL-7 inhibits in vitro spontaneous apoptosis in T-cell ALL probably through BCL-2 up-regulation. They also found that IL-7 induced inhibition of apoptosis correlated to a better early cytoreduction in patients with ALL. Yada, et al, [Yada, 2001] have shown that IL-7 inhibits the spontaneous apoptosis of i-IEL (intestinal intraepithelial lymphocytes) by inhibiting caspase-dependent and caspase-independent pathways. We have found that the inhibition of cell growth mediated by rapamycin is partially due to apoptosis. Other mechanisms must be present to cause the profound growth arrest seen with rapamycin. Also, we have observed that IL-7 is capable of reversing rapamycin's inhibitory effect in pre-B ALL cells, but the effect is dose dependent both on IL-7 dose and rapamycin dose. These data demonstrate that the two pathways intersect at some point, with p27kip1 a likely candidate. Rapamycin inhibits the degradation of p27kip1 via mTOR preventing cell cycle progression whereas IL-7 signaling in T cells and T-ALL cells has been shown to lead to p27kip1 degradation leading to cell cycle progression. An alternative explanation is that the mTOR pathways and IL-7 mediated signaling pathways co-exist within progenitor B cells. Rapamycin-induced inhibition of mTOR pathway then allows for the IL-7R signaling pathway to play a more dominant role within a cell. There is a balance of survival and apoptotic signals. When rapamycin is present, the apoptotic or cell arrest signals dominate whereas when IL-7 is present, then the survival signals predominate and the apoptotic signals are attenuated.

In summary, the mTOR inhibitor, rapamycin, demonstrates activity against pre-B ALL both in vitro and in vivo using a leukemic mouse model. Moreover, IL-7-mediated signaling appears to play a role in sustaining cell survival and thus contributing to the transforming process of early precursor B cells.

Example II

Evaluation of Changes in mRNA Expresion in ALL Cells Treated with Rapamycin with and without IL-7

In order to assess more broadly the mechanism of action of rapamycin and the effect of IL-7 on these cells, we used Affymetrix MG-U74Av4 Genechips to evaluate changes in mRNA expression. In ALL cells treated with rapamycin +/−IL-7, we found clustering of differential expression of genes involved in cell metabolism, growth and survival as well as genes involved in transcription and translation regulation. We found the most profound change in expression in the YES proto-oncogene, a member of the src family of kinases. It is virtually undetectable in cells treated with rapamycin, and is completely rescued with the addition of IL-7. To characterize the post-translational changes that occur within ALL cell lines when cultured with rapamycin and IL-7, we evaluated proteins known to play a role in mTOR and IL-7 signaling pathways. Phosphorylated p70S6 kinase is profoundly decreased in rapamycin-treated cells, while the level of phosphor-p70S6 kinase is restored to baseline with the addition of IL-7. These results suggest that one regulatory point common to both pathways may be the phosphorylation of p70S6 kinase. However, the ability of IL-7 to reverse rapamycin-induced growth inhibition may involve other target proteins downstream of p70S6 kinase, such as p27kip1 or cdk2. In summary, these data demonstrate that 1) mTOR inhibitors are active against B-precursor malignancies; 2) IL-7 reverses rapamycin-induced inhibition; and 3) p70S6 kinase is a key regulator of both the inhibitor effect of rapamycin and the stimulatory effect of IL-7.

Example III

RAD001 is Active Against Leukemia in Experimental Models of ALL

In this study, we have found that a second mTOR inhibitor, RAD001 (everolimus) (Novartis), also causes growth suppression in ALL cells in vitro as well as showing activity in vivo against leukemia/lymphoma in the ALL mouse model. RAD001 inhibits growth >50–90% in ALL cell lines. Daily oral administration of RAD001 extends survival almost 4 fold in Eμ-RET+ mice with advanced leukemia (high white blood count, large nodal masses, and massive hepatosplenomegaly) as compared to untreated littermates. In addition to extending survival, RAD001 induces disappearance of nodal masses and normalization of peripheral WBC counts. These results are similar to those found with rapamycin. These data demonstrate that the mTOR inhibitors rapamycin and RAD001 are both active against B-precursor malignancies.

Example IV

A Phase I Trial of Sirolimus in Relapsed/Refractory Leukemia and Non-Hodgkin's Lymphoma Although the prognosis for acute leukemia and non-Hodgkin'lymphoma has improved over the past several decades, the prognosis for children with recurrent disease is poor. At present children who have bone marrow or combined bone marrow and extramedullary relapses of acute leukemia while on therapy have a 5–20% of long-term survival. For children with bone marrow relapse off therapy the prognosis is improved, with a 20–50% long-term survival. Long-term survival rate in children with relapsed NHL is dismal, with less than 20% achieving long term survival. Newer, targeted agents need to be identified and integrated into the present cytotoxic chemotherapy regimens.

Sirolimus was initially developed as an immunosuppressive agent because it inhibits T-lymphocyte proliferation that occurs in response to antigenic and cytokine stimulation. In vivo, sirolimus binds to other proteins to generate an immunosuppressive complex that binds to and inhibits the activation of the mammalian target of sirolimus (mTOR). The inhibition of mTOR's protein kinase activity inhibits a variety of signal transduction pathways including production of proteins that regulate the cell cycle. Sirolimus inhibits the progression of lymphocytes from the G1-to-S phase. This may provide synergy with other cytotoxic agents which inhibit activity at alternative points in the cell cycle. Preclinical data show that sirolimus inhibits the growth of B-precursor ALL lines in vitro and has activity in a murine model of

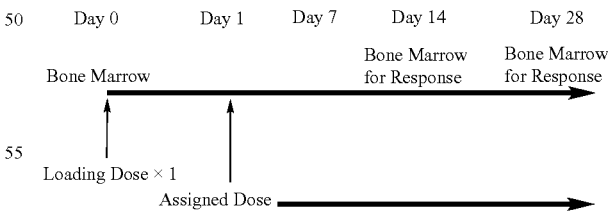

leukemia/lymphoma. Sirolimus (rapamycin), a mTOR inhibitor, was approved by the FDA for use after solid organ transplant in 1999. It is commercially available as Rapamune® oral solution 1 mg/mL and 1 mg tablets from Wyeth-Ayerst Laboratories.

Described hereinbelow is a Phase I dose finding study for the maximum tolerated dose (MTD) of oral sirolimus, given as a single daily oral dose.

Experimental Design Schema

This study will enable us to 1) to define the maximum tolerated dose (MTD) of oral sirolimus administered daily to children with refractory or relapsed leukemia or non-Hodgkin'lymphoma; 2) to determine the dose-limiting toxicities (DLT) of oral sirolimus given on this schedule; 3) to characterize the trough levels produced by administration of oral sirolimus in children with refractory/relapsed leukemia or non-Hodgkin's lymphoma; 4) to assess the anti-leukemia/lymphoma activity of sirolimus within the confines of a Phase I study; and 5) to evaluate the effect of sirolimus on intracellular targets, including p70/S6 kinase (a marker of mTOR inhibition), phosphoAKT, P27kip1, and STAT5 in peripheral blood mononuclear cells, peripheral blood lymphoblasts, and bone marrow lymphoblasts.

The pharmacokinetics of sirolimus have been studied in healthy subjects, pediatric dialysis patients, hepatically-impaired adult patients, and adult renal transplant patients. Oral doses of both liquid and solid sirolimus are rapidly, though variably, absorbed. Mean time-to-peak concentrations range from 1 hour in healthy subjects to 2 hours in renal transplant recipients. Half-life is upwards of 2½ days. Metabolism is by the intestinal and hepatic CYP3A4 enzyme family and 91% of the elimination of the drug is via the GI tract. The AUC correlates well with trough and peak concentrations. Patients who ingested the drug after a high fat breakfast did have delayed $C_{max}$ and it is recommended to consistently take sirolimus with or without food.

In a Phase I pharmacokinetic study conducted in renal transplant patients doses ranging from 0.5 to 6.5 mg/m$^2$ were administered every 12 hours. Phase III studies to date have had concomitant use of cyclosporine, steroid, or both. At a dose of 2 mg/day the sirolimus trough concentration was 8.58+/−4.0 ng/ml and at 5 mg/day the trough was 17.3+/−7.4 ng/ml. Sirolimus concentrations in stable renal transplant patients are dose proportional between 3 and 12 mg/m$^2$. Also, in this population a loading dose of 3 times the maintenance dose provided near steady-state concentrations within 1 day in most patients. Stable renal transplant recipients have received single doses of up to 21 mg/m$^2$. No toxicity has been observed in any of several single dosing studies with sirolimus doses ranging from 3–21 mg/m$^2$.

In pediatric dialysis patients, young patients 5–11 years, exhibited greater oral clearances and shorter half-lives. This suggests that they may need higher doses per body weight or surface area than adults. Patients 12 to 18 years had similar PK parameters as adult renal transplant patients. The variability of bioavailability in the pediatric group may be overcome by obtaining trough serum levels, which are readily available at the Hospital of University of Pennsylvania Toxicology Laboratory.

Studies in Transplant

The safety and efficacy of sirolimus in the prevention of organ rejection have been demonstrated in two randomized, double-blind, multicenter, controlled trials involving over 1000 adult patients. Typical dosing was 2 mg or 5 mg administered daily. In these and most trials sirolimus has been administered with cyclosporine and corticosteroids and limited PK data is available with sirolimus alone in this setting.

The major side effects noted in these studies included thrombocytopenia, hypercholesteremia, hypertriglyceridemia, and diarrhea. Renal function was not worse in these patients.

In February of 2001 the Cooperative Clinical Trials in Pediatric Renal Transplantation opened a study of Sirolimus, in lieu of traditional calcineurin inhibitors, combined with corticosteroids and mycophenolate mofetol, (MMF) in living donor pediatric kidney transplantation. The study uses a loading dose of 10 mg/m$^2$ followed by subsequent doses of 3 mg/m$^2$ divided BID given dailly. Doses are adjusted by trough levels with goal trough levels being 20–25 ng/ml. Personal communication with the Children's Hospital of Philadelphia principal investigator reveals that initial trough levels are often slightly lower than goal. Toxicities noted to date that would meet Common Toxicity Criteria (CTC) of Grade III and IV, include stomatitis, hypercholesteremia, and hypertriglyceridemia.

A Phase II pilot study of Cyclophosphamide, Rituximab, and Sirolimus in the treatment of EBV associated post-transplant lymphoproliferative disease (PTLD) has been open at CHOP since October 2001. Dosing is lower for this study because the drug is being given with Rituximab and Cyclophosphamide. No children have met enrollment criteria to date.

Patient Eligibility and Study Entry

Inclusion Criteria

IV.1.1 Age <21 years at the time of study entry.

IV.1.2 Histologic Diagnosis

Patients must have documented recurrent or refractory acute lymphoblastic leukemia (ALL) or acute myeloblastic leukemia (AML) with ≧25% blasts in the marrow. Patients with non-Hodgkin's lymphoma (NHL) must have radiologic or physical evidence of recurrence. Patients must have experienced their second or greater relapse.

IV.1.3 Patient must have a disease for which there is no known curative therapy.

IV.1.4 Karnofsky ≧50% for patients ≧10 years of age and Lansky ≧50 for children <10 years of age.

IV.1.5 Life Expectancy ≧4 weeks.

IV.1.6 Informed Consent/Assent

IV.1.7 Patient must be able to consume oral medication in the form of tablets or solution.

Exclusion Criteria

IV.2.1 Pregnancy or Breast-Feeding

Pregnancy tests must be obtained in females of childbearing potential. Pregnant or lactating patients are ineligible for this study due to the unknown human fetal or teratogenic toxicities of sirolimus. Males or females of reproductive age may not participate unless they have agreed to use an effective contraceptive method.

IV.2.2 Patients Who Have An Uncontrolled Infection

Patients must have any active infection under control. Fungal disease must be stable for at least 2 weeks before enrollment. Patients with bacteremia must have a documented negative blood culture prior to initiating drug.

IV.2.3 Patients Who Do Not Meet Organ Function Requirements Per Section 2.5

IV.2.4 Patients Currently Receiving Other Investigational Anti-Neoplastic Drugs

IV.2.5 Patients who have a known allergy to sirolimus, FK506, or other mTOR inhibitors are not eligible.

Prior Therapy

Patients must have fully recovered from the acute toxic effects of all prior chemotherapy, immunotherapy, or radiotherapy prior to entering this study. Patients must have recovered from the non-hematologic toxic effects of all prior therapy before entry into this trial. Recovery is defined as a toxicity grade <2 as defined by the Common Toxicity Criteria Version 2.0, unless otherwise specified in the Inclusion and Exclusion criteria.

Myelosuppressive chemotherapy must not have been received within 2 weeks of entry onto this study (4 weeks if prior nitrosourea). Patients may have received hydroxyurea OR corticosteroids if they have had stable or rising peripheral blast counts for three days. The study PI must be contacted for any child who has received steroids or hydroxyurea within 2 weeks of enrollment. Patients must not have been treated for at least 7 days with a biologic anti-neoplastic agent.

XRT: ≧2 wks for local palliative XRT (small port); ≧4 weeks must have elapsed if prior craniospinal XRT or if ≧50% radiation of pelvis; ≧4 wks must have elapsed if other substantial BM radiation.

Bone Marrow Transplant (BMT)/Stem Cell Transplant (SCT): No evidence of active graft vs. host disease. For allogeneic BMT/SCT, ≧3 months must have elapsed.

Concomitant Medications

Hematopoietic growth factor(s): Must not have received within 1 week of entry onto this study except for erythropoietin.

Steroids: Patients may have received corticosteroids within two weeks of entry if they have had stable or rising peripheral blast counts for three days. The study PI must be contacted prior to enrollment. If corticosteroids were administered for life threatening superior vena cava syndrome or spinal cord compression, the patient may enroll when medically stable.

Hydroxyurea: Patients may have received hydroxyurea within two weeks of entry if they have had stable or rising peripheral blast counts for three days. The study PI must be contacted prior to enrollment.

Organ Function Requirements

Adequate Bone Marrow Function Defined as:

Patients with ALL, AML, and NHL patients with tumor metastatic to bone marrow, who have granulocytopenia, anemia, and/or thrombocytopenia are eligible, but will not be evaluable for hematological toxicity.

For patients with NHL including status post SCT:
Peripheral absolute neutrophil count (ANC) ≧1000/μL
Platelet count ≧75,000/μL (transfusion independent)
Hemoglobin ≧8.0 gm/dL (may receive RBC transfusions)

Adequate Renal Function Defined as:
Creatinine clearance or radioisotope GFR ≧70 ml/min/m$^2$ OR
A serum creatinine based on age is shown in Table II

TABLE II

Serum Creatinine Criteria Based on Age

| Age (Years) | Maximum Serum Creatinine (mg/dL) |
|---|---|
| <5 | 0.8 |
| 5 > age ≦ 10 | 1.0 |
| 10 > age ≦ 15 | 1.2 |
| >15 | 1.5 |

Adequate Liver Function Defined as:
Total bilirubin ≦1.5×normal for age, and
SGPT (ALT) ≦5×normal for age and albumin ≧2 g/dL.

Adequate Cardiac Function Defined as:
Shortening fraction of ≧28% by echocardiogram, or
Ejection fraction of ≧50% by gated radionuclide study.

Treatment Program

Study description: This is a Phase I, open label, dose escalation study of a daily regimen of sirolimus at four or more dose levels in pediatric patients with relapsed leukemia or NHL. 24–30 patients who are eligible may be enrolled into the study. 3–6 patients will be enrolled into each dose group. A single dose group may be expanded by 3 additional patients to further evaluate safety. The dose determined to be the MTD will accrue a total of 6 ALL and 6 AML patients to further evaluate safety and assess biological endpoints.

Treatment

Loading Dose

All patients will receive a loading dose on day 0, time 0. Subsequent dosing at the assigned dose level will start 24 hours following the initial loading dose.

Sirolimus

Starting 24 hours after the initial loading dose, patients will take the assigned dose daily. The drug is taken continuously, with no rests. See Section 5.0 for dosing modifications.

Extramedullary Disease

Patients with CNS and bone marrow involvement of ALL, AML, or CNS involvement of NHL, may receive concomitant intrathecal chemotherapy with IT cytarabine and IT hydrocortisone. Radiation therapy should not be administered, except for emergent situations or persistent extramedullary disease with resolution of bone marrow disease (until the patient is in a CRp or CR).

Dose Escalation

TABLE III

Dose Escalation Schedule

| Dose Levels | Loading Dose (mg/m$^2$) | Dose (mg/m$^2$) |
|---|---|---|
| Dose Level 1 | 9 mg/m$^2$ | 3 mg/m$^2$/day |
| Dose Level 2 | 12 mg/m$^2$ | 4 mg/m$^2$/day |
| Dose Level 3 | 16 mg/m$^2$ | 5.2 mg/m$^2$/day |
| Dose Level 4 | 20 mg/m$^2$ | 6.8 mg/m$^2$/day |

*Any further escalation will be in increments of 30%

If the MTD is exceeded at the first dose level, then the subsequent cohort of patients will not receive a loading dose and will be treated at a dose that is 30% lower than the starting dose (2 mg/m$^2$/day).

Inter-Patient Escalation

All patients will receive a one-time loading dose. The starting dose will then be 3 mg/m$^2$/day to start 24 hours after the loading dose. Dose levels for subsequent groups of patients is based on escalation in increments of 30%, using the dose escalation rules specified in Section 4.2. A cycle will be considered 28 days. There is no limit to the duration of use if the patient is maintaining a PR/CRp/CR.

Intra-Patient Escalation

No intra-patient escalation will be permitted.

Required Observations/Material and Data to be Accessioned

Clinical and Laboratory Studies

All entry/eligibility studies must be performed within 1 week prior to entry onto the trial (unless otherwise specified). Imaging studies are required within 1 month prior to study entry.

TABLE IV

Clinical and Laboratory Study Schedule

| STUDIES TO BE OBTAINED | Pre-Study | Course 1 | Subsequent Courses | Off Study |
|---|---|---|---|---|
| History | X | | | |
| Physical Exam (Ht, Wt, BSA, VS) | X | Weekly | X | X |
| Performance Status | X | | | X |
| CBC, differential, platelets | X | Twice Weekly | Weekly | X |
| Pharmacokinetics* | X | X | | |
| Urinalysis | X | | | |
| Electrolytes including Ca++, PO₄, Mg++, Cr, ALT, AST, bilirubin ■ | X | 1–3 × per week ■ | X | X |
| Cholesterol/Triglyceride levels | X | X | X | X |
| Pregnancy Test** | X | | | |
| Tumor Disease Evaluation | X | Day 14, 28 ● ● | X | X |
| Bone Marrow Aspirate or Biopsy (Response) | X | Day 14, 28 ● ● | X*** | X |
| Spinal Tap | X | | | |
| Echocardiogram ■ ■ | X | | | |
| Bone Marrow Biology Studies | X | Day 7 ● ●, 14, 28 | | X |
| Peripheral Blood Biology Studies | X | D 3, 7, 14, 28 | | |
| TROUGH Sirolimus Level | X | D 3, 7, 28 | Monthly | |

OBTAIN OTHER STUDIES AS NEEDED FOR GOOD PATIENT CARE
*See Section 6.2 for timing of PK studies.
**Patients of childbearing potential require a negative pregnancy test prior to starting treatment.
***If a patient obtains a CR or CRp on the cycle 1, day 28 bone marrow, bone marrows only need to be performed if there is suspicion/evidence of relapse. The on-study bone marrow may be up to 14 days prior to enrollment
■ Tumor lysis labs (electrolytes, BUN, Cr, Ca, PO₄, and uric acid) should be obtained 3× in the first week. If there is no evidence of tumor lysis, obtain weekly chemistries as outlined above.
■ ■ On study echocardiogram needs to be obtained within 4 weeks of study entry
● Response will be evaluated at Day 28 of cycle 1 (see Section 10.0)
● ● The Day 7 Bone marrow may be replaced by peripheral blood if the patient has a peripheral leukemic blast count >5,000/ml.

Pharmacology

Description of Assay

Plasma Sirolimus levels will be determined by commercially available assay.

Sampling Schedule

Sirolimus levels will be obtained just prior to the loading dose, and should also be obtained prior to the am dose on days 3, 7, and 28. If the drug is held for toxicity a level should be sent. Levels should be obtained monthly and if drugs that are metabolized through CYP 3A4 are added to the patients regimen.

Sample Collection and Handling Instructions

3–4 cc in a purple top (EDTA) tube to be sent to central dispatch for shipment to the commercial assay laboratory. Record the exact time that the sample is drawn along with the exact time that the drug was administered. This should be a TROUGH level: patients should be advised NOT to take the sirolimus prior to the clinic appointment.

Statistical Considerations

Sample Size and Study Duration

This trial is a phase I evaluation of sirolimus with the starting dose and schedule as stated in Section 4.0. A minimum of 3 evaluable patients will be entered at each dose level. Review of the entry rate into previous new agent studies indicates that 1 patient per month is available which will permit completion of the study within 24 months. A maximum of 30 patients is anticipated.

Statistical Analysis

Clinical Trial Analysis

Patient characteristics such as age, gender, ethnicity, disease, and disease status, will be tabulated with descriptive statistics. All severe adverse events will be tabulated. The overall and disease specific percentage of patients responding will be calculated with-95% confidence intervals. Kaplan-Meier analysis will be used to describe the time to disease progression for patients receiving sirolimus.

Biology Study Analysis

The presence of p70/S6 kinase, phospho-AKT, p27kip1 and STAT5 will be assayed in leukemic blasts at day 0, day 3, and day 7, if peripheral blasts remain present. These signaling intermediates will also be assessed in peripheral blood mononuclear cells. Expression levels of these molecules will be quantified by gel densitometry and described with summary statistics. Levels of expression on will be compared with paired t-tests.

Definitions

Evaluable For Toxicity

Dose escalation will not be considered until at least 3 evaluable patients have been entered at the current dose level. For the purpose of dose escalation, all 3 patients in a given cohort must have been treated for at least 28 days, or had progressive disease, before another dose level is initiated.

Maximum Tolerated Dose

The MTD will be that dose at which fewer than one-third of patients experience DLT.

Dose Escalation

Escalations are planned in groups of three patients, with an additional three patients to be added at the first indication of DLT. The following dose escalation rules will be used:
1. 3 patients are studied at the first dose level.
2. If none of these 3 patients experience DLT within 28 days, then the dose is escalated to the next higher level in the 3 subsequent patients.
3. If 1 of 3 patients experiences DLT at the current dose, then up to 3 more patients are accrued at the same level.
   a) If none of these 3 additional patients experience DLT, then the dose is escalated in subsequent patients.
   b) If one or more of these 3 additional patients experiences DLT, then patient entry at that dose level is stopped, the MTD has been exceeded and dose escalation will be stopped. Up to 9 more patients are treated at the next lower dose, with a goal of having 6 AML and 6 ALL patients treated at the MTD.
4. If two or more patients experience DLT, then the MTD has been exceeded and dose escalation will be stopped. Up to 9 more patients are treated at the next lower dose, with a goal of having 6 AML and 6 ALL patients treated at the MTD.
5. The MTD is the dose level at which 0/3 or 1/6 patients experience DLT with at least 2/3 or 2/6 patients encountering DLT at the next higher dose.

Example V

Rapamycin for Immunosuppression and B Cell Modulation post Matched Sibling Donor Marrow Transplant for Acute Lymphoblastic Leukemia This study will enable us to 1) to evaluate toxicity of rapamycin (sirolimus, Rapamune®) when used for post-bone marrow transplant graft vs. host disease prophylaxis in children with acute lymphoblastic leukemia (ALL); 2) to evaluate acute and chronic graft vs. host disease (GVHD) incidence and severity in patients receiving rapamycin for immunoprophylaxis post BMT; 3) to evaluate overall survival and event free survival in patients receiving rapamycin as GVHD prophylaxis after matched related bone marrow transplant for relapsed ALL; and 4) to evaluate intracellular targets of the rapamycin effect, including p70s6 kinase and P27kip1, as well as STAT5, in peripheral blood lymphocytes of BMT patients.

In bone marrow transplant studies, sirolimus is effective in reducing mortality from GVHD in MHC mismatched donor-recipient combinations. This may be due to T cells that are calcium independent and resistant to cyclosporine, but can be blocked by sirolimus. Sirolimus also appears effective in preventing graft rejection, facilitating allogeneic engraftment and accelerating hematopoietic recovery. Sirolimus accelerated hematopoietic recovery in one study using murine recipients of T cell depleted marrow. Sirolimus has also been studied in patients with GVHD. In a pilot trial of 21 patients with steroid refractory severe acute GVHD, oral sirolimus was used. Eleven patients completed the 14 day course of Sirolimus. 28% of all patients enrolled had a response, but toxicities were noted which necessitated discontinuation of drug in 5 patients. The most common side effects noted included thrombocytopenia and neutropenia, elevated serum triglycerides and cholesterol (these lipid effects are also seen with cyclosporine). Hemolytic uremic syndrome developed in 5 patients, and this has been noted in renal allograft recipients when the dose of cyclosporine is not reduced during Sirolimus administration, as was the case in this group.

Sirolimus and similar drugs (mTOR inhibitors) have been shown to inhibit growth of mature B and T lymphocytes, and there is preclinical evidence of activity of these drugs in mature B cell lymphomas. The National Cancer Institute is currently sponsoring a phase II lymphoma treatment using a Sirolimus analogue. Sirolimus may block cell cycle progression of B cells and increase their apoptotic rate at doses used for immunosuppression. Preliminary studies suggest that Sirolimus is active against B cell precursor lymphoid malignancies, as well, with inhibition of B precursor ALL lines in vitro and activity in a murine model of leukemia/lymphoma. Rapamycin has been shown to prevent the endogenous expression of p27kip1, and to block in vivo phosphorylation of Rb protein leukemic T cells on IL-7 mediated signal transduction.

The anti-cancer mechanism of sirolimus and its analogues is unique, and currently under extensive study and development. The use of sirolimus in in vivo mouse models shows inhibition of metastatic tumor growth at doses used for immunosuppression. Antiangiogenic properties that may decrease the risk of recurrent cancers has been demonstrated. Both human and murine pre-B ALL cell lines have shown inhibition of growth in culture when treated with Sirolimus. At least some of the inhibitory effect of sirolimus is due to induction of apoptosis.

Oral doses of both liquid and solid sirolimus are rapidly, though variably, absorbed. Metabolism is by the intestinal and hepatic CYP3A enzyme family. The AUC correlates well with trough and peak concentrations. In pediatric renal transplant recipients, young patients 5–11 years exhibited greater oral clearances, which suggests that they may need higher doses per body weight or surface area than adults. The half-life of sirolimus was shorter and clearance greater in this study. The variability of bioavailability in the pediatric group may be overcome by obtaining trough serum levels, which are readily available at the Hospital of University of Pennsylvania Toxicology Laboratory. In studies of renal transplant recipients who received Sirolimus in addition to CSA, thrombocytopenia (platelets $<150\times10^3/mm^2$ and leukopenia appear to be related to high trough concentrations. Most resolve spontaneously, and those that don't, respond to dose reduction.

Allogeneic Bone Marrow Transplantation for Children with ALL

Children who have very high risk features, such as t(4;11) or t(9;22), or those who relapse while on chemotherapy are rarely cured by chemotherapy alone. These patients, as well as those beyond second remission, are generally referred for allogeneic stem cell transplantation. Approximately 25–30% of these patients will have a matched sibling donor. Matched sibling donor bone marrow transplant results in approximately 40–60% of patients surviving disease free, but relapse remains the largest obstacle to cure. Rapamycin, with its apoptotic effects upon B cell precursor malignancies, may prove effective in decreasing the incidence of relapse in these patients, particularly when used in a state of minimal residual disease post transplant. We expect to treat approximately 4 patients with ALL yearly with matched related donor BMT at CHOP.

Sirolimus will be substituted for cyclosporine once initial engraftment occurs, and patients are able to take oral medications. Its use is two fold: attempt to achieve an anti-B cell precursor effect (see above), and prevent graft vs. host disease (GVHD). With cyclosporine, acute GVHD develops in approximately 40% of pediatric matched related donor recipients, and the majority is mild and easily controllable by the addition of methylprednisolone or prednisone. At CHOP, "short course" methotrexate in addition to CSA is given only to patients >14 years, or those with older donors. Chronic GVHD occurs in approximately 20% of pediatric matched related donor recipients, and 75% of this is limited to skin. Therefore, the use of sirolimus in this group may accomplish adequate immunosuppression so as to prevent GVHD, as well as provide anti-B and anti-T cell malignancy effect. Sirolimus may also prove less toxic than the calcineurin inhibitors as well, in which both nephrotoxicity and neurotoxicity remain serious side effects.

Eligibility Requirements
1. Patients with lymphoid malignancies considered for allogeneic stem cell transplant:
   First remission:
   if remission not achieved by day28
   high risk cytogenetic features, including t(9;22) or t(4;11)
   Second or third remission
2. HLA-identical sibling donor available for marrow donation.
3. Organ criteria
   a. Cardiac: ECHO shortening fraction >27%
   b. Renal: Creatinine clearance >60 ml/min/1.73 m$^2$
   c. Hepatic: Bilirubin <1.5 mg/dl, transaminases <3×normal
   d. Infection: no active infection, HIV negative
4. Consents signed by parent or guardian. Assent when age appropriate.

Therapy
A. Conditioning:
   1. Thiotepa 5 mg/kg days −7, −6. Given IV over 4 hours with routine supportive care.
   Cyclophosphamide 60 mg/kg days −5, −4. Given over 1 hour IV with routine supportive care.
   2. Total body irradiation 200 cGy/fraction×6 fractions given over 3 days. Testicular boost 400 cGy for males. Patients with prior CNS disease and no prior CNS irradiation: 600 cGy prior to starting conditioning.
B. GVHD prophylaxis (initial)
   1. Cyclosporine A 3 mg/kg/day by continuous infusion beginning at day-1. Target serum levels between 300–400 ng/dl.
   2. Patients >14 years and/or donors >14 years: Methotrexate 15 mg/m$^2$ day +1; 10 mg/m$^2$ days +3, 6. Hold if transaminases >10×normal or bilirubin >2 mg/dl.
C. Rapamycin immunomodulation
   1. Day +21–28 (depending upon oral medication tolerance): Stop cyclosporine unless evidence GVHD. Begin oral sirolimus with dosing as follows:
   <40 kg: 1 mg/m$^2$/day
   ≧40 kg: 2 mg/day
   2. Drug should be administered consistently with or without food. Do not give with grapefruit juice.
   3. Drug levels: Obtain trough sirolimus level the following day and daily until target steady state concentration of 9–12-ng/ml reached.
   As CSA levels leave tissue compartments, sirolimus levels may lower due to removal of CSA effect on sirolimus clearance.
D. GVHD: If GVHD develops prior to day +21, begin methylprednisolone 2 mg/kg/day as per SCT routine.
   1. GVHD resolved by day +28: stop CSA, and begin sirolimus as above.
   2. Persistent GVHD at day +28: Decrease CSA to obtain trough 150–200 ng/dl (Neoral) or 200–300 ng/dl (IV CSA) and begin sirolimus. Continue methylprednisolone.
   3. Progressive GVHD at day +21: Management as per SCT physician. Patient off study.
E. Immunosuppression weaning.
   1. Prednisone to be weaned off first, if being used. Wean by 10–20% weekly, depending upon response.
   2. Absent GVHD: begin Sirolimus wean at day +100–110. Wean by 10% weekly.
F. Modification for toxicity:
   1. Cytopenias: these may be related to GVHD or other drugs routinely given to patients post BMT. Sirolimus may be discontinued and CSA substituted for ANC<500 or new onset thrombocytopenia if there is concern that these are caused by Sirolimus. Other causes such as other drugs or relapse, should be considered as well.
G. Laboratory Studies
   1. Routine: Comprehensive chemistry panels twice weekly (inpatient) and once weekly as outpatient for first 3 months post BMT. Panels done weekly-every other week after 3 months.
   Electrolytes, BUN, creatinine: daily as inpatient.
   Cyclosporine levels: every 3–7 days depending upon serum level, creatinine.
   2. Sirolimus levels (5 ml): after starting:
   Trough level morning after starting drug.
   Trough level every 3–7 days after adjustments until target level reached.
   Additional level 3 days after starting maintenance dose.
   Weekly levels until weaning commenced.
   Sirolimus levels will be done instead of CSA levels, which are routinely done weekly. If both drugs are used, then levels of both will be obtained.
   For Sirolimus levels: Target steady state concentration of 9–12 ng/mL.
   3. Laboratory correlation:
   To evaluate intracellular targets of sirolimus, 5–10 cc of peripheral blood will be drawn from the patient's central venous catheter on admission for BMT (prior to any drug administration) and on day 1, 3 and 7 of sirolimus administration. Peripheral blood lymphocytes will be isolated and assessed for inhibition of p70s6 kinase, p27kip1 and STAT5. Blood will be obtained at the same time as blood is obtained for other routine clinical studies. Total blood will be 20–40 ml/patient.
   Patient ≦20 kg: 5 ml
   Patient>20 kg: 10 ml Statistical Analysis
The frequency and severity of all toxicity events will be tabulated with summary statistics. Toxicity will be assessed by the CTC standard toxicity criteria. The frequency and grade of acute GVHD at 100 days and chronic GVHD at 12 months will be tabulated with summary statistics. The overall survival and event free survival will be estimated by Kaplan-Meier analysis.

Data and Safety Monitoring

A. Stopping Rules:
All serious adverse events will be promptly reported to the IRB. Analysis will occur on an ongoing basis to ensure adherence to stopping rules. Transplant related mortality for matched sibling donor transplant is approximately 15%, a mortality rate that is acceptable given the poor prognosis of these patients without BMT.
   A.1 Stopping Rules for Toxicity
The following stopping rules are based on an expected trial size of 12 patient accrued over 3 years. Clinical experience with sirolimus in solid organ transplant patients provides good evidence that sirolimus will not have significantly more or serious side effects than cyclosporine. Patients receiving cyclosporine as GVHD prophylaxis in MRD BMT may experience severe adverse events from the cyclosporine; this risk is modified by the patient's condition prior to transplant. In the setting of MRD BMT for relapsed ALL, 10–20% of patients may experience adverse events with cyclosporine. Given the baseline risk of cyclosporine in this patient population and the absence of other curative therapies for these patients, a 10 to 20% risk of an adverse event attributed to sirolimus is acceptable.

With this background, the following Table V represents the probabilities of more than "X" events over a range of "true" toxicity rates.

TABLE V

Stopping Toxicity Rules

| True Toxicity rate | Total patients (N) | Events (R) | Probability of >R events |
|---|---|---|---|
| .10 | 12 | 1 | 0.34 |
| .10 | 12 | 2 | 0.12 |
| .10 | 12 | 3 | 0.03 |
| .20 | 12 | 1 | 0.73 |
| .20 | 12 | 2 | 0.45 |
| .20 | 12 | 3 | 0.21 |

Thus, if the true severe adverse event rate is 10%, there is a 12% probability that more than 2 patients will experience a severe adverse event. If the true toxicity rate is 20%, then there is a 45% probability that more than 2 patients will experience a severe adverse event. Thus, if 2 patients experience a severe adverse event related to sirolimus, then it is likely that the true severe adverse event rate is greater than 20% and the study will be closed.

A.2 Stopping Rules for Excessive GVHD:

Clinical experience with MRD BMT indicates that the risk of acute GVHD is approximately 40% with the risk of grade III or IV acute GVHD is approximately 20%. The risk of chronic GVHD is approximately 20%, with the risk of extensive chronic GVHD is approximately 10–20%. For this study, we consider an acute GVHD rate of greater than 30% to be unacceptable and a chronic GVHD rate of greater than 25% to be unacceptable. The following tables describe the number of separate acute and chronic GVHD events needed at each number of anticipated patients to give a 80% chance that the acute GVHD rate exceeds 30% and that the chronic GVHD rate exceeds 25%.

TABLE VI

Acute GVHD Stopping Rules

| Accetable Acute GVHD rate | Total patients (N) | Events (R) | Probability of >30% Acute GVHD rate |
|---|---|---|---|
| .30 | 2 | 1 | .80 |
| .30 | 3–5 | 2 | .80 |
| .30 | 6–8 | 3 | .80 |
| .30 | 9–11 | 4 | .80 |

TABLE VII

Chronic GVHD Stopping Rules

| Accetable Chronic GVHD rate | Total patients (N) | Events (R) | Probability of >25% Chronic GVHD rate |
|---|---|---|---|
| .25 | 2–3 | 1 | .80 |
| .25 | 3–6 | 1 | .80 |
| .25 | 7–7 | 3 | .80 |
| .25 | 10–11 | 4 | .80 |

Clearly, the foregoing methods should decrease post bone marrow transplant graft vs. host disease associated with this modality of treatment for refractory ALL, thereby improving the prognosis for these children.

REFERENCES

1. Vogler, L. B., Crist, W. M., Bockman, D. E., Pearl, E. R., Lawton, A. R. & Cooper, M. D. (1978) N Engl J Med 298, 872–878.
2. LeBien, T. W. (2000) Blood 96, 9–23.
3. Loken, M. R., Shah, V. O., Dattilio, K. L. & Civin, C. I. (1987) Blood 70, 1316–1324.
4. Cronin, F. E., Jiang, M., Abbas, A. K. & Grupp, S. A. (1998) J Immunol 161, 252–259.
5. Stoddart, A., Flemming, H. E. & Paige, C. J. (2000) Immunol Rev 175, 47–58.
6. Ichihara, M., Iwamoto, T., Isobe, K., Takahashi, M., Nakayama, A., Pu, M., Dai, Y., Parashar, A., Ohkus, K. & Kato, M. (1995) Br J Cancer 71, 808–813.
7. Wasserman, R., Li, Y. S. & Hardy, R. R. (1995) J Immunol 155, 644.
8. Goodfellow, P. J. & Wells, S. A. J. (1995) J Natl Cancer Inst 87, 1515.
9. Iwamoto, T., Pu, M., Ito, M., Takahashi, M., Isobe, K., Nagase, F., Kawashima, K., Ichihara, M. & Nakashima, I. (1991) European Journal of Immunology 21, 1809–1814.
10. Wasserman, R., Zeng, X. X. & Hardy, R. R. (1998) Blood 92, 273–282.
11. Zeng, X.-X., Zhang, H., Hardy, R. R. & Wasserman, R. (1998) Blood 92, 3529–3536.
12. Hayakawa, K., Li, Y. S., Wasserman, R., Sauder, S., Shinton, S. & Hardy, R. R. (1997) Ann N Y Acad Sci 815, 15–29.
13. Appasamy, P. M. (1999) cytokines, cellular and molecular therapy 5, 25–39.
14. Page, T. H., Lali, F. V. & Foxwell, B. M. J. (1995) European Journal of Immunology 25, 2956–2960.
15. Hofineister, R., Khaled, A. R., Benbernou, N., Rajnavolgyi, E., Muegge, K. & Durum, S. K. (1999) Cytokine Growth Factor Rev 10, 41–60.
16. Pribyl, J. A. & LeBien, T. W. (1996) Proc Natl Acad Sci USA 93, 10348–10353.
17. Dittel, B. N. & LeBien, T. W. (1995) J Immunol 155, 58–67.
18. Smart, F. M. & Venkitaraman, A. R. (2000) J Exp Med 191, 737–742.
19. Uckun, F. M., Tuel-Ahlgren, L., Obuz, V., Smith, R., Dibirdik, I., Hanson, M., Langlie, M. C. & Ledbetter, J. A. (1991) Proc Natl Acad Sci USA 88, 6323–6367.
20. Sato, A. K., Yanai, N., Okubo, T., Mori, K. J. & Obinata, M. (2001) Cell Struct Function 26, 95–101.
21. van der Plas, D.C., Smiers, F., Pouwels, K., Hoefsloot, L. H., Lowenberg, B. & Touw, I. P. (1996) Leukemia 10, 1317–1325.
22. Dadi, H. K. & Roifman, C. M. (1993) J Clin Invest 92, 1559–1563.
23. Dadi, H. K., Ke, S. & Roifman, C. M. (1993) Biochem Biophys Res Commun 192, 459–464.
24. Dadi, H. & Roifman, C. M. (1994) Blood 84, 1579–1586.
25. Seckinger, P. & Fougereau, M. (1994) J Immunol 153, 97–109.
26. Karawajew, L., Wuchter, C., Kosser, A., Schrappe, M., Dorken, B. & Ludwig, W.-D. (2000) Blood 96, 297–306.
27. Wuchter, C., Ruppert, V., Schrappe, M., Dorken, B., Ludwig, W. D. & Karawajew, L. (2002) Blood 99, 4109–4115.

28. Touw, I., Pouwels, K., van Agthoven, T., van Gurp, R., Budel, L., Hoogerbrugge, H., Delwel, R., Goodwin, R. G., Namen, A. E. & Lowenberg, B. (1990) *Blood* 75, 2097–2101.

29. Barata, J. T., Cardoso, A. A., Nadler, L. M. & Boussiotis, V. A. (2001) *Blood* 98, 1524–1531.

30. Foss, H. D., Hummel, M., Gottstein, S., Ziemann, K., Falini, B., Herbst, H. & Stein, H. (1995) *Am J Pathol* 146, 33–39.

31. Benjamin, D., Sharma, V., Knobloch, T. J., Armitage, R. J., Dayton, M. A. & Goodwin, R. G. (1994) *J Immunol* 152, 4749–4757.

32. Renard, N., Duvert, V., Matthews, D. J., Pages, M.-P., Magaud, J.-P., Manel, A.-M., Pandrau-Garcia, D., Philippe, N., Banchereau, J. & Saeland, S. (1995) *Leukemia* 9, 1219–1226.

33. Bierer, e. a. (1990) *PNAS* 87, 9231–9235.

34. Wicker, L. S., Boltz, R. C., Matt, V., Nichols, E. A., Peterson, L. B. & Sigal, N. H. (1990) *Eur J Immunol* 20, 2277–2283.

35. Kay, J. E., Kromwel, L., Doe, S. E. A. & Denyer, M. (1991) *Immunology* 72, 544–549.

36. Sakata, A., Kuwahara, K., Ohmura, T., Inui, S. & Sakaguchi, N. (1999) *Immunol Lett* 68, 301–309.

37. Morris, R. E. (1991) *immunology today* 12, 137–140.

38. Ettenger, R. B. & Grimm, E. M. (2001) *Am J Kidney Dis* 38, S22–28.

39. Saunders, R. N., Metcalfe, M. S. & Nicholson, M. L. (2001) *Kidney Int* 59, 3–16.

40. Calne, R. Y., Collier, D. S., Lim, S., Pollard, S. G., Samaan, A., White, D. J. & Thiru, S. (1989) *Lancet* 2, 227.

41. Schreiber, S. L. (1991) *Science* 251, 283–287.

42. Huang, S. & Houghton, P. J. (2002) *Curr Opin Investig Drugs* 3, 295–304.

43. Huang, S. & Houghton, P. J. (2001) *Drug Resist Updat* 4, 378–391.

44. Elit, L. (2002) *Curr Opin Investig Drugs* 3, 1249–1253.

45. Hidalgo, M. & Rowinsky, E. K. (2000) *Oncogene* 19, 6680–6686.

46. Garber, K. (2001) *J Natl Cancer Inst* 93, 1517–1519.

47. Castedo, M., Ferri, K. F. & Kroemer, G. (2002) *Cell Death Differ* 9, 99–100.

48. Brunn, G. J., Hudson, C. C., Sekulic, A., Williams, J. M., Hosoi, H., Houghton, P. J., Lawrence, J. C. & Abraham, R. T. (1997) *Science* 277, 99–101.

49. Burnett, P. E., Barrow, R. K., Cohen, N. A., Snyder, S. H. & Sabatini, D. M. (1998) *Proc Natl Acad Sci USA* 95, 1432–1437.

50. West, M. J., Stoneley, M. & Willis, A. E. (1998) *Oncogene* 17, 769–780.

51. Raught, B., Gingras, A. C. & Sonenberg, N. (2001) *Proc Natl Acad Sci USA* 98, 7037–7044.

52. Dumont, F. J., Altmeyer, A., Kastner, C., Fischer, P. A., Page Lemon, K., Chung, J., Blenis, J. & Staruch, M. J. (1994) *J Immunol* 152, 992–1003.

53. Kuo, C. J., Chung, J., Fiorentino, D. F., Flanagan, W. M., Blenis, J. & Crabtree, G. R. (1992) *Nature* 358, 70–73.

54. Chen, Y., Chen, H., Rhoad, A. E., Warner, L., Caggiano, T. J., Failli, A., Zhag, H., Hsiao, C.-L., Nakanishi, K. & Molnar-Kimber, K. L. (1994) *Biochem Biophys Res Commun* 203, 1–7.

55. Brown, E. J., Albers, M. W., Shin, T. B., Ichikawa, K., Keith, C. T., Lane, W. S. & Schreiber, S. L. (1994) *Nature* 369, 756–758.

56. Degiannis, D. & Hornung, N. (1995) *Transplantation* 59, 1076–1079.

57. Li, H.-L., Davis, W. & Pure, E. (1999) *J Biol Chem* 274, 9812–9820.

58. Mosmann, T. (1983) *J Immunol Methods* 65, 55–63.

59. Kim, J. M., Alcorn, K., Fang, J., Brown, V. I. & Grupp, S. A. (2002) *AACR Meeting*.

60. MacDonald, A., Scarola, J., Burke, J. T. & Zimmerman, J. J. (2000) *Clin Ther* 22 Suppl B, B101–121.

61. Hacein-Bey-Abina, S., von Kalle, C., Schmidt, M., Le Deist, F., Wulffraat, N., McIntyre, E., Radford, I., Villeval, J. L., Fraser, C. C., Cavazzana-Calvo, M., et al. (2003) *N Engl J Med* 348, 255–256.

62. Gaynon, P. S., Qu, R. P., Chappell, R. J., Willoughby, M. L., Tubergen, D. G., Steinherz, P. G. & Trigg, M. E. (1998) *Cancer* 82, 1387–1395.

63. Chessells, J. M. (1998) *Br J Haematol* 102, 423–438.

64. Wei, C., Zeff, R. & Goldschneider, I. (2000) *J Immunol* 164, 1961–1970.

65. Yehuda, A. B., Wirtheim, E., Abdulhai, A., Or, R., Slavin, S., Babaey, S. & Friedman, G. (1999) *Journals of Gerontology* 54, B143–148.

66. Hacein-Bey-Abina, S., Le Deist, F., Carlier, F., Bouneaud, C., Hue, C., De Villartay, J. P., Thrasher, A. J., Wulffraat, N., Sorensen, R., Dupuis-Girod, S., et al. (2002) *N Engl J Med* 346, 1185–1193.

67. Cavazzana-Calvo, M., Hacein-Bey, S., de Saint Basile, G., Gross, F., Yvon, E., Nusbaum, P., Selz, F., Hue, C., Certain, S., Casanova, J. L., et al. (2000) *Science* 288, 669–672.

68. Fischer, A. (2002) *Scand J Immunol* 55, 238–241.

69. Fischer, A. (2000) *Clin Exp Immunol* 122, 143–149.

70. Cavazzana-Calvo, M., Hacein-Bey, S., Yates, F., de Villartay, J. P., Le Deist, F. & Fischer, A. (2001) *J Gene Med* 3, 201–206.

71. Yada, S., Nukina, H., Kishihara, K., Takamura, N., Yoshida, H., Inagaki-Ohara, K., Nomoto, K. & Lin, T. (2001) *Cell Immunol* 208, 88–95.

72. Weng, Q. P., Kozlowski, M., Belham, C., Zhang, A., Comb, M. J. & Avruch, J. (1998) *J Biol Chem* 273, 16621–16629.

73. Guba, M., von Breitenbuch, P., Steinbauer, M., Koehl, G., Flegel, S., Hornung, M., Bruns, C. J., Zuelke, C., Farkas, S., Anthuber, M., et al. (2002) *Nat Med* 8, 128–135.

74. (2000) *Schalm's Veterinary Hematology Manual* (Lippincott, Williams, & Wilkins, Phialdephia).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a patient having an early B cell acute lymphoblastic leukemia (ALL) comprising administering to said patient a therapeutically effective amount of rapamycin or a derivative thereof and a therapeutically effective amount of an IL-7 inhibitor, wherein said rapamycin or derivative thereof inhibits the mammalian target of rapamycin (mTOR).

2. The method of claim 1, wherein said patient is newly diagnosed with early B cell ALL.

3. The method of claim 1, wherein said patient is experiencing refractory or relapsed early B cell ALL.

4. The method of claim 1, wherein said rapamycin or derivative thereof and said IL-7 inhibitor are administered, simultaneously or sequentially.

5. The method of claim 1, wherein said IL-7 inhibitor is an IL-7 specific antibody or a fragment thereof.

6. The method of claim 1, further comprising administering at least one anti-cancer agent selected from the group consisting of alkylating agents, bifunctional alkylating agents, non-steroidal aromatase inhibitors, immunotherapeutic agents, nitrosurea compounds, antimetabolites, anti-tumor antibiotics, mitotic inhibitors, radiation, topoisomerase I inhibitors, and anti-estrogens.

7. The method of claim 1, further comprising administering at least one anti-cancer agent selected from the group consisting of cisplatin, carboplatin, oxaliplatin, radiation, CPT-11, paclitaxel, 5-flourouracil, leucovorin, epothilone, gemcitabine, UFT, herceptin, cytoxan, dacarbaxine, ifosfamide, mechlorethamine, melphalan, chlorambucil, anastrozole, exemstane, carmustine, lomustine, methotrexate, gemcitabine, cytarabine, fludarabine, bleomycin, dactinomycin, daunorubicin, doxorubicin, idarubicin, docetaxel, vinblastine, vincristin, vinorelbine, topotecan, lupron, megace, leucovorin, Iressa, flavopiridol, immunomotherapeutic agents, ZD6474, SU6668, and valspodar.

8. The method of claim 1, wherein said patient is experiencing refractory or relapsed early B-cell ALL following a bone marrow transplant (BMT), and wherein said administration of a therapeutically effective amount of rapamycin or a derivative thereof inhibits graft versus host disease.

9. The method of claim 8, wherein said rapamycin is administered in combination with at least one other immunosuppression agent.

10. The method of claim 8, wherein said rapamycin or a derivative thereof is administered post said BMT.

11. The method of claim 8, further comprising administering to said patient a therapeutic effective amount of at least one immunosuppressant prior and/or post said BMT.

* * * * *